US009090941B2

(12) United States Patent
Barany et al.

(10) Patent No.: US 9,090,941 B2
(45) Date of Patent: Jul. 28, 2015

(54) USE OF LECITHIN:RETINOL ACYL TRANSFERASE GENE PROMOTER METHYLATION IN EVALUATING THE CANCER STATE OF SUBJECT

(75) Inventors: Francis Barany, New York, NY (US); Yu-Wei Cheng, Forest Hills, NY (US); Philip Paty, New York, NY (US); Daniel Notterman, Cranbury, NJ (US)

(73) Assignees: Cornell Research Foundation, Inc., Ithaca, NY (US); Sloan Kettering Institute for Cancer Research, New York, NY (US); Rutgers, The State University of New Jersey, New Brunswick, NJ (US)

( * ) Notice: Subject to any disclaimer, the term of this patent is extended or adjusted under 35 U.S.C. 154(b) by 1405 days.

(21) Appl. No.: 12/520,386

(22) PCT Filed: Dec. 19, 2007

(86) PCT No.: PCT/US2007/088116

§ 371 (c)(1), (2), (4) Date: Feb. 12, 2010

(87) PCT Pub. No.: WO2008/077095

PCT Pub. Date: Jun. 26, 2008

(65) Prior Publication Data

US 2010/0144867 A1 Jun. 10, 2010

Related U.S. Application Data

(60) Provisional application No. 60/870,765, filed on Dec. 19, 2006.

(51) Int. Cl.

*C12Q 1/68* (2006.01)
*C12P 19/34* (2006.01)
*C07H 21/02* (2006.01)

(52) U.S. Cl.

CPC ........ *C12Q 1/6886* (2013.01); *C12Q 2600/106* (2013.01); *C12Q 2600/118* (2013.01); *C12Q 2600/154* (2013.01); *C12Q 2600/16* (2013.01)

(58) Field of Classification Search

CPC ........... C12Q 1/6886; C12Q 2600/154; C12Q 2600/118; C12Q 2521/331; C12Q 2523/125; C12Q 2600/106; G01N 2800/52; G01N 33/57419

See application file for complete search history.

(56) References Cited

U.S. PATENT DOCUMENTS

| | | | |
|---|---|---|---|
| 6,200,756 | B1 | 3/2001 | Hermann et al. |
| 6,706,506 | B2 | 3/2004 | Gudas et al. |
| 6,811,982 | B2 | 11/2004 | Gonzalgo et al. |
| 6,858,388 | B2 | 2/2005 | Markowitz et al. |
| 7,022,472 | B2 | 4/2006 | Robbins et al. |
| 2005/0227265 | A1 | 10/2005 | Barany et al. |

FOREIGN PATENT DOCUMENTS

| | | | |
|---|---|---|---|
| WO | 2006084051 | A2 | 8/2006 |
| WO | 2008087040 | A2 | 7/2008 |

OTHER PUBLICATIONS

Ruiz A. et al. The Journal of Biological Chemistry vol. 274, No. 6, Issue of Feb. 5, pp. 3834-3841, 1999.*

GenBank Locus AC009567 (May 25, 2000) *Homo sapiens* chromosome 4, clone RP11-21G20, complete sequence, from www.ncbi.nlm.nih.gov, pp. 1-43.*

GenBank Locus AY546085 (Oct. 13, 2004) *Homo sapiens* lecithin:retinol acyltransferase isoform 1 (LRAT) mRNA, complete cds., from www.ncbi.nlm.nih.gov, pp. 1-3.*

Juppner H. Bone vol. 17, No. 2, Supplement, Aug. 1995:39S-42S.*

Song F. et al. PNAS (Mar. 1, 2005),vol. 102, No. 9, pp. 3336-3341.*

Costello J.F. et al. The Journal of Biological Chemistry (1994) vol. 269, No. 25, p. 17228-17237.*

Search report dated Oct. 27, 2010 for corresponding European Patent Application No. 07869512.9.

Guo et al., "Retinol Metabolism and Lecithin: Retinol Acyltransferase Levels are Reduced in Cultured Human Prostate Cancer Cells and Tissue Specimens," Cancer Res. 62:1654-1661 (2002).

Guo et al., "Esterification of All-Trans-Retinol in Normal Human Epithelial Cell Strains and Carcinoma Lines from Oral Cavity, Skin and Breast: Reduced Expression of Lecithin: Retinol Acyltransferase in Carcinoma Lines," Carcinogenesis 21(11):1925-1933 (2000).

Dew et al., "Effects of Pharmacological Retinoids on Several Vitamin A-Metabolizing Enzymes," Cancer Res. 53:2965-2969 (1993).

Kelloff et al., "Chemopreventive Drug Development: Perspectives and Progress," Cancer Epidemiol. Biomarkers Prev. 3:95-98 (1994).

Chansri et al., "Inhibition of Liver Metastasis by All-Trans Retinoic Acid Incorporated into O/W Emulsions in Mice," Int. J. Pharm. 321:42-49 (2006).

Boorjian et al., "Reduced Lecithin: Retinol Acyltransferase Expression Correlates with Increased Pathologic Tumor Stage in Bladder Cancer," Clin. Cancer Res. 10:3429-3437 (2004).

Zhan et al., "Differential Expression of the Enzyme that Esterifies Retinol, Lecithin: Retinol Acyltransferase, in Subtypes of Human Renal Cancer and Normal Kidney," Clin. Cancer Res. 9:4897-4905 (2003).

(Continued)

*Primary Examiner* — Stephen Kapushoc
(74) *Attorney, Agent, or Firm* — LeClairRyan, a Professional Corporation

(57) ABSTRACT

The present invention relates to a method of evaluating the cancer state of a subject using lecithin:retinol acyl transferase (LRAT) gene promoter methylation status. Methods of analyzing and quantifying LRAT gene promoter methylation level are also disclosed. The present invention also relates to methods of determining the prognosis for s subject having cancer by assessing LRAT mRNA expression and LRAT protein expression. Methods of cancer detection, diagnosis, prognosis, and treatment are also disclosed.

16 Claims, 22 Drawing Sheets

(56) References Cited

OTHER PUBLICATIONS

Nagasaka et al., "Hypernnethylation of O6-Methylguanine-DNA Methyltransferase Promoter may Predict Nonrecurrence after Chemotherapy in Colorectal Cancer Cases," Clin. Cancer Res. 9:5306-5312 (2003).

International Preliminary Report on Patentability for PCTUS2007088116 dated Jun. 24, 2009.

Written Opinion for PCTUS2007088116 dated Oct. 7, 2008.

International Search Report dated Oct. 7, 2008.

Zhan et al., "Differential Expression of the Enzyme That Esterifies Retinol, Lecithin:Retinol Acyltransferase, in Subtypes of Human Renal Cancer and Normal Kidney," Clinical Cancer Research 9:4897-4905 (2003).

* cited by examiner

Bisulfite/PCR-PCR/LDR/Universal Array

1. Treat DNA with sodium bisulfite to convert unmethylated, but not methylated cytosines into uracils. Only the cytosines present in CpG sites are shown here.
2. The resultant strands are not complementary. PCR amplify one strand using gene-specific/ universal primers and Taq polymerase. ◆
3. PCR amplify the complementary strand of the first PCR synthesis using gene-specific/ universal primers (A) and Taq polymerase. ◆
4. PCR ammplify all primary products using universal primers and Taq polymerase. ◆
5. Perform LDR using primers specific for converted unmethylated and methylated sequence, and thermostable ligase. ●
6. Capture fluorescent products on addressable array and score for presence of unmethylated DNA (control) as well as methylated.

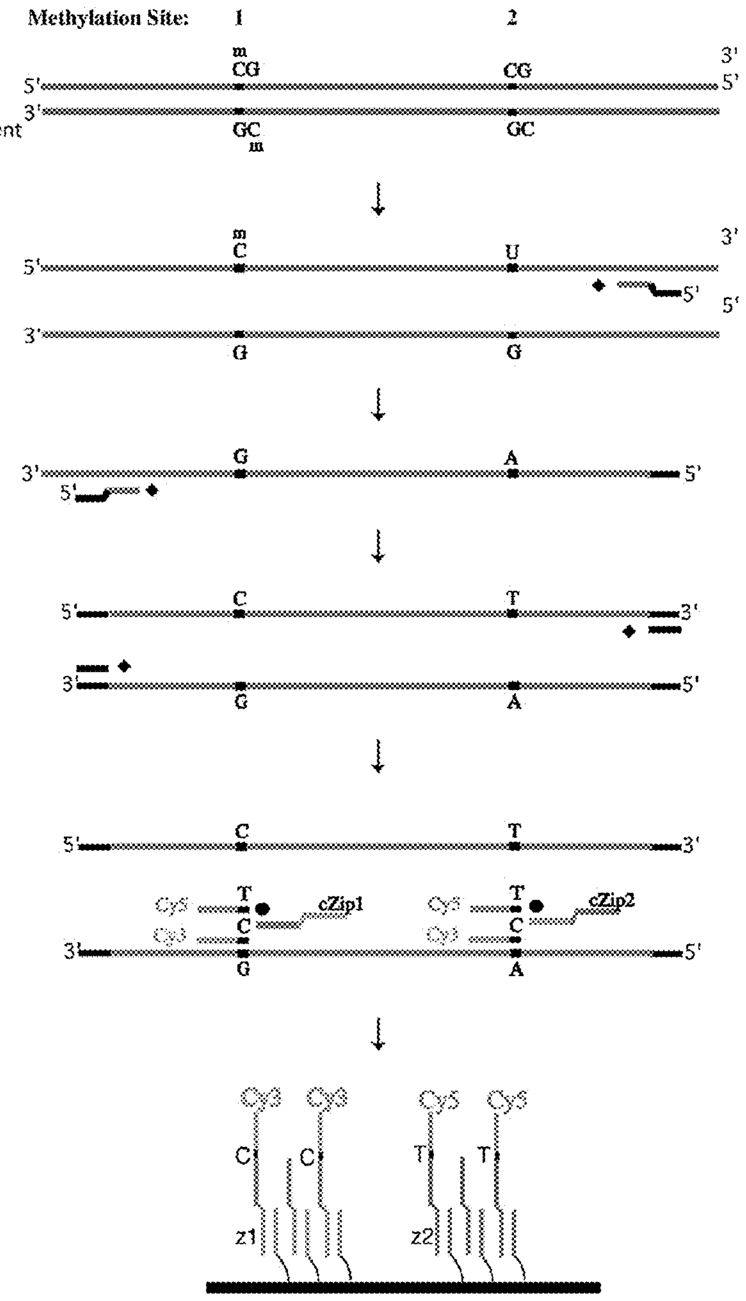

Address Zip1 identifies methylated cytosine in methylation site 1, and address Zip2 identifies unmethylated cytosines in methylation site 2.

Figure 2

Bisulfite/PCR-PCR/LDR/Capillary Electrophoresis

Bisulfite/ PCR-PCR/ LDR/ Dual Universal Array

1. Treat DNA with sodium bisulfite to convert unmethylated, but not methylated cytosines into uracils. Only the cytosines present in CpG sites are shown here.

2. The resultant strands are not complementary. PCR amplify one strand using gene-specific/ universal primers and Taq polymerase. ◆

3. PCR amplify the complementary strand of the first PCR synthesis using gene-specific/ universal primers (A) and Taq polymerase. ◆

4. PCR ammplify all primary products using universal primers and Taq polymerase. ◆

5. Perform LDR using primers specific for either converted unmethylated or methylated sequence, and thermostable ligase. ●

6. Capture fluorescent products on two separated addressable arrays and score for the presence of methylated DNA as well as unmethylated.

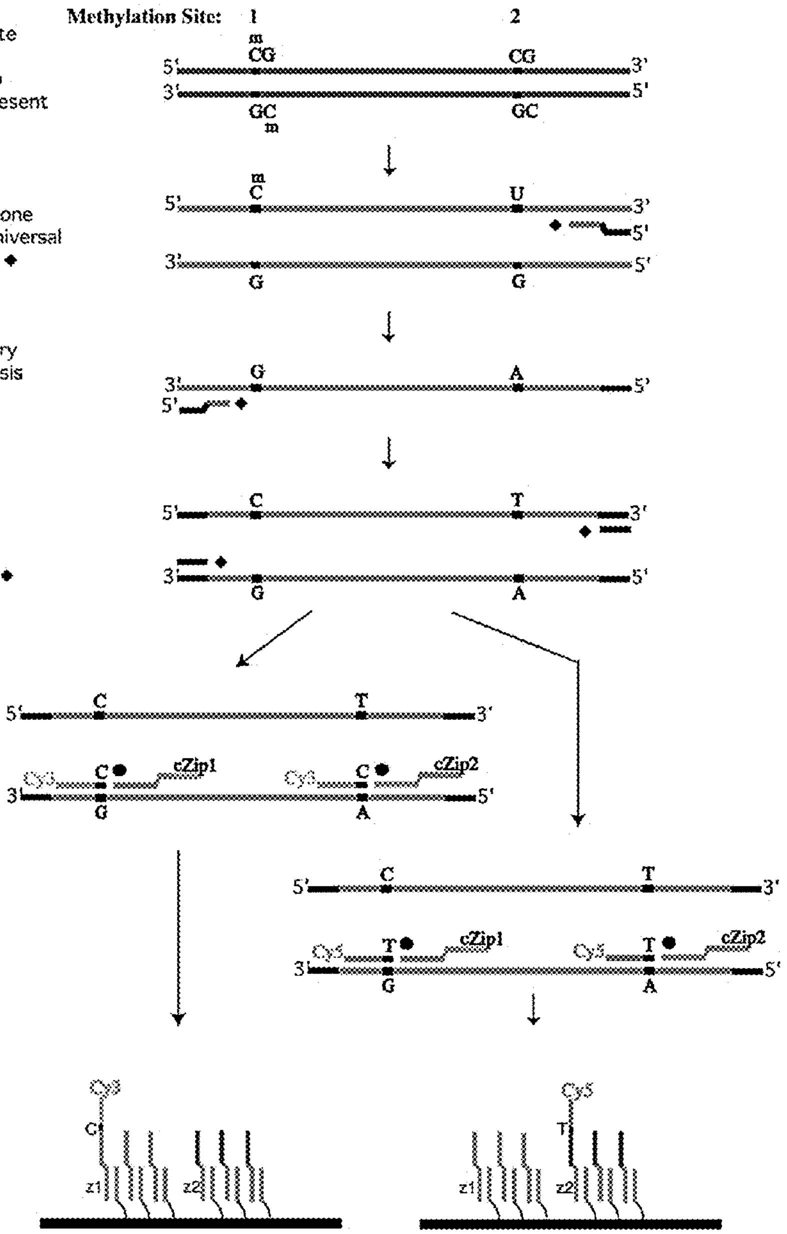

Address Zip1 identifies methylated cytosine in methylation site 1.

Address Zip2 identifies unmethylated cytosine in methylation site 2.

Figure 4

Bisulfite/ PCR-PCR/ LDR/ Universal Array: Nucleotide Analogs

1. Treat DNA with sodium bisulfite to convert unmethylated, but not methylated cytosines into uracils. Only the cytosines present in CpG dinucleotide sites are shown here.
2. The resultant strands are not complementary. PCR amplify one strand using gene-specific/universal primers and Taq polymerase. ◆
3. PCR amplify the complementary strand of the first PCR synthesis using gene-specific/ universal primers (A) and Taq polymerase. ◆
4. PCR ammplify all primary products using universal primers and Taq polymerase. ◆
5. Perform LDR using primers specific for converted unmethylated and methylated sequence, and thermostable ligase. ●
6. Capture fluorescent products on addressable array and score for presence of unmethylated DNA (control) as well as methylated.

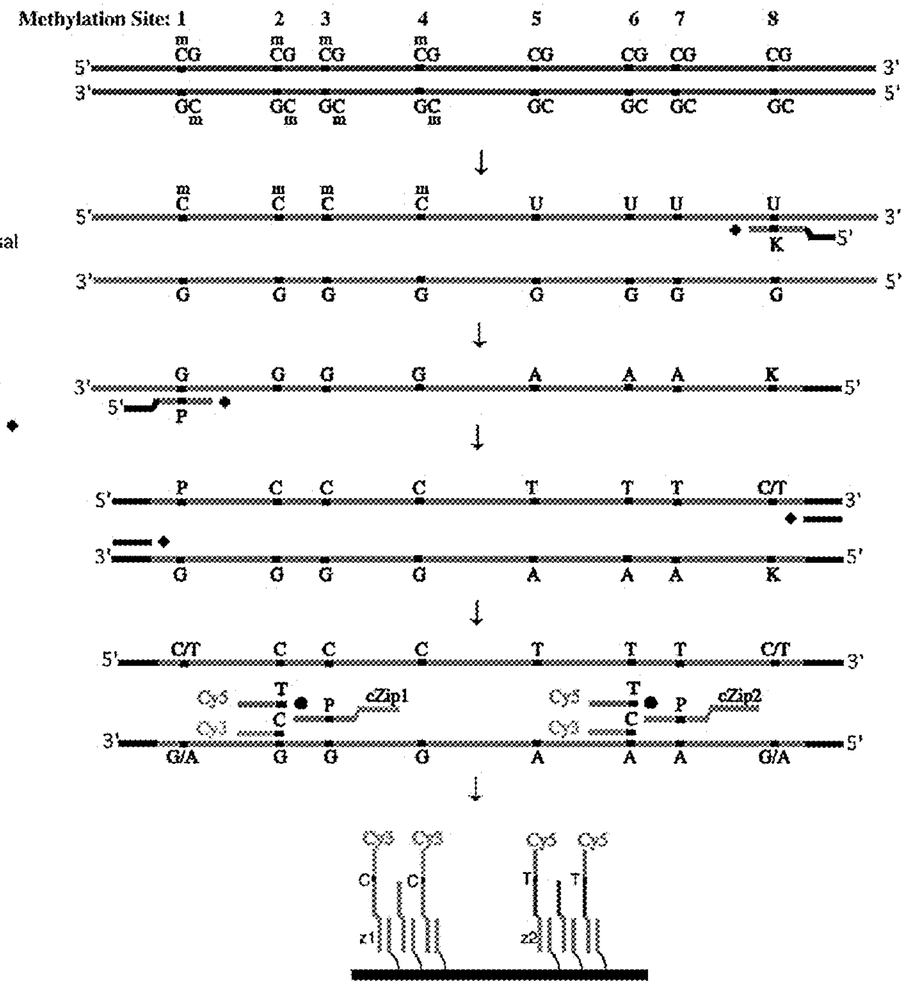

Address Zip1 identifies methylated cytosine in methylation site 2, and address Zip2 identifies unmethylated cytosines in methylation site 6.

Figure 5

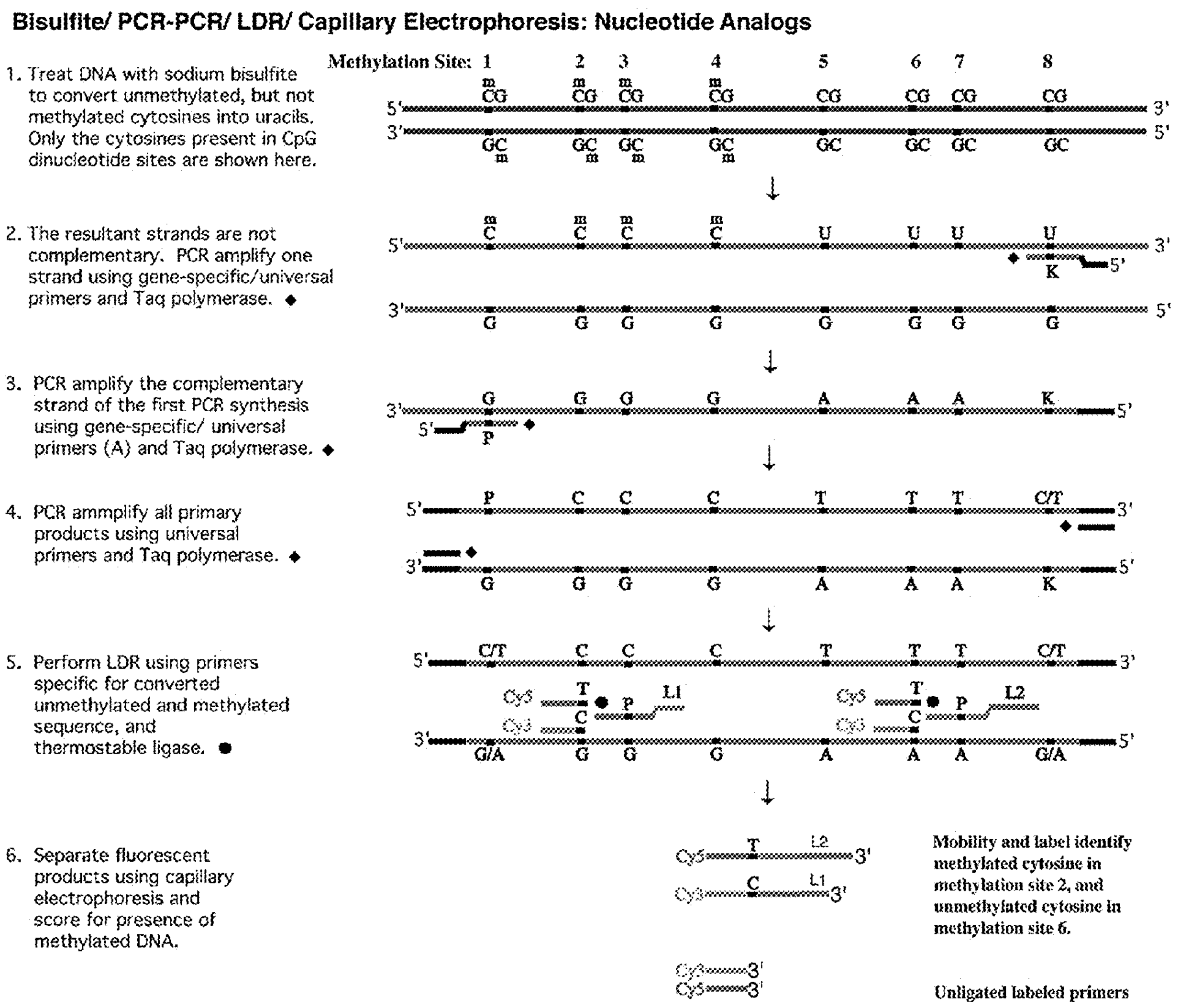

Figure 6

Bisulfite/ PCR-PCR/ LDR/ Capillary Electrophoresis: Nucleotide Analogs

1. Treat DNA with sodium bisulfite to convert unmethylated, but not methylated cytosines into uracils. Only the cytosines present in CpG dinucleotide sites are shown here. ◆

2. The resultant strands are not complementary. PCR amplify one strand using gene-specific/universal primers and Taq polymerase. ◆

3. PCR amplify the complementary strand of the first PCR synthesis using gene-specific/ universal primers (A) and Taq polymerase. ◆

4. PCR ammplify all primary products using universal primers and Taq polymerase. ●

5. Perform LDR using primers specific for converted unmethylated and methylated sequence, and thermostable ligase. ●

6. Separate fluorescent products using capillary electrophoresis and score for presence of methylated DNA.

Bisulfite/ PCR-PCR/ LDR/ Universal Array: Preferential for Methylated DNA

1. Treat DNA with sodium bisulfite to convert unmethylated, but not methylated cytosines into uracils. Only the cytosines present in CpG dinucleotide sites are shown here.

2. The resultant strands are not complementary. PCR amplify one strand using gene-specific/universal primers and Taq polymerase. ◆

3. PCR amplify the complementary strand of the first PCR synthesis using gene-specific/ universal primers (A) and Taq polymerase. ◆

4. PCR ammplify all primary products using universal primers and Taq polymerase. ◆

5. Perform LDR using primers specific for converted unmethylated and methylated sequence, and thermostable ligase. ●

6. Capture fluorescent products on addressable array and score for presence of unmethylated DNA (control) as well as methylated.

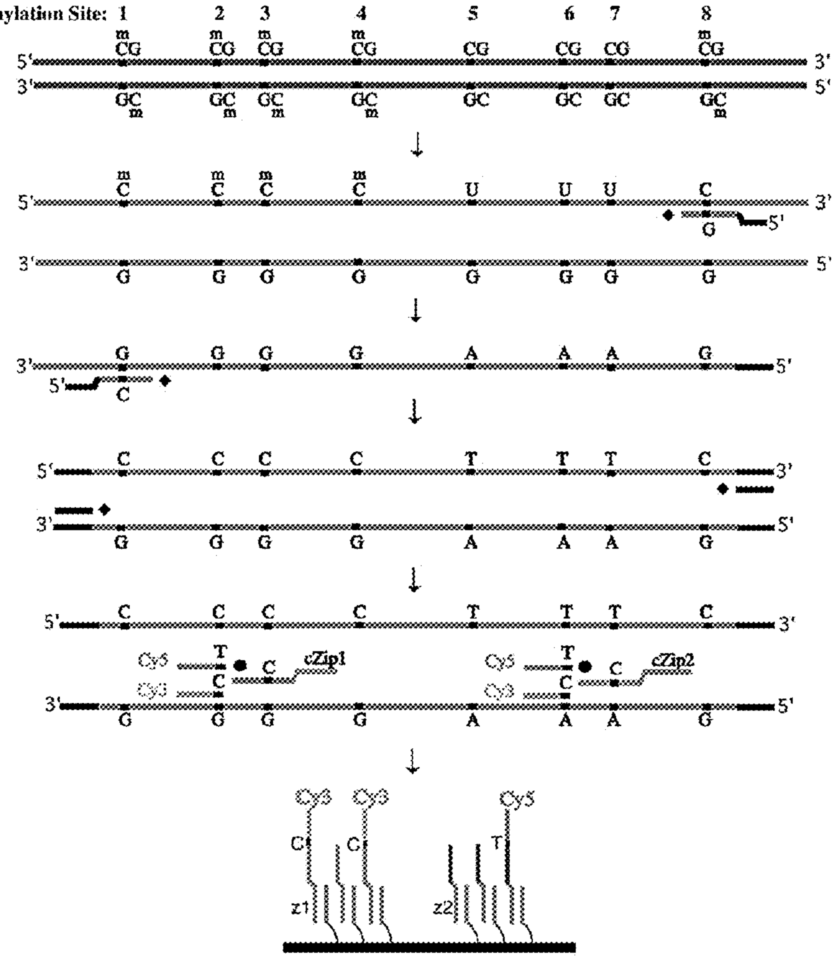

Address Zip1 identifies methylated cytosine in methylation site 2, and address Zip2 identifies unmethylated cytosines in methylation site 6.

Figure 7

Organization of human LRAT gene

LRAT promoter region

```
gcccccaggt gcgctccttc tccggctgct tgtagcactg gtctcactgt ccccgccgtc    60
agccaccggt tccttatccg tctcattccc cattgtggct tggctgagcc ggtcgccagg   120
cctcgctgtc ctcctttgcc ttcctctctc ctcagcggcc gtactttgcg ccgtacctca   180
cctggcctgc aggtgagcag cagcgcagca cccctgcccg gcgagcttaa cttgcccagc   240
ccggcccctg ccggagtggc accggcacct ctccaagacg ccctcttccc tgcaggATGA   300
AGAACCCCAT GCTGGAGGTG GTGTCTTTAC TACTGGAGAA GCTGCTCCTC ATCTCCAACT   360
TCACGCTCTT TAGTTCGGGC GCCGCGGGCG AAGACAAAGG GAGGAACAGT TTTTATGAAA   420
CCAGCTCTTT CCACCGAGGC GACGTGCTGG AGGTGCCCCG GACCCACCTG ACCCACTATG   480
GCATCTACCT AGGAGACAAC CGTGTTGCCC ACATGATGCC CGACATCCTG TTGGCCCTGA   540
CAGACGACAT GGGGCGCACG CAGAAGGTGG TCTCCAACAA GCGTCTCATC CTGGGCGTTA   600
TTGTCAAAGT GGCCAGCATC CGCGTGGACA CAGTGGAGGA CTTCGCCTAC GGAGCTAACA   660
TCCTGGTCAA TCACCTGGAC GAGTCCCTCC AGAAAAAGGC ACTGCTCAAC GAGGAGGTGG   720
CGCGGAGGGC TGAAAAGCTG CTGGGCTTTA CCCCCTACAG CCTGCTGTGG AACAACTGCG   780
AGCACTTCGT GACCTACTGC AGATATGGCA CCCCGATCAG TCCCCAGTCC GACAAggtat   840
gatgtgtgac tcccagggga agtgggctcc gcggagatgc cccctcccat ccctgacctt   900
ttctcttccc cgcgagtagg gatctaattc ctggacacct cccctaccac              950
```

Figure 12A

Methylation levels of Colorectal Cancer samples

| Sample ID | Tissue | Site 1 | Site 2 | Site 3 | Site 4 | Site 5 | Site 6 | Site 7 | Site 8 | Site 9 | Site 10 | Ave. Site1-6 | Methylation Score |
|---|---|---|---|---|---|---|---|---|---|---|---|---|---|
| 02184A | Primary tumor | 0.31 | 0.22 | 0.10 | 0.03 | 0.18 | 0.15 | 0.23 | 0.18 | 0.28 | 0.35 | 0.17 | 0.00 |
| C0161A | Primary tumor | 0.03 | 0.06 | 0.01 | 0.00 | 0.01 | 0.03 | 0.44 | 0.35 | 0.40 | 0.39 | 0.02 | 0.00 |
| C0331A | Primary tumor | 0.15 | 0.11 | 0.06 | 0.03 | 0.09 | 0.07 | 0.02 | 0.13 | 0.06 | 0.26 | 0.08 | 0.00 |
| C0575A | Primary tumor | 0.19 | 0.12 | 0.02 | 0.06 | 0.05 | 0.04 | 0.30 | 0.14 | 0.26 | 0.37 | 0.08 | 0.00 |
| 05708A | Primary tumor | 0.25 | 0.23 | 0.03 | 0.07 | 0.08 | 0.11 | 0.45 | 0.26 | 0.44 | 0.47 | 0.13 | 0.00 |
| 05839A | Primary tumor | 0.48 | 0.46 | 0.23 | 0.31 | 0.15 | 0.18 | 0.26 | 0.39 | 0.50 | 0.46 | 0.30 | 1.00 |
| 06706A | Primary tumor | 0.45 | 0.46 | 0.42 | 0.43 | 0.46 | 0.41 | 0.50 | 0.42 | 0.50 | 0.46 | 0.44 | 1.00 |
| 07925A | Primary tumor | 0.41 | 0.36 | 0.11 | 0.11 | 0.16 | 0.14 | 0.25 | 0.25 | 0.29 | 0.38 | 0.22 | 1.00 |
| 07930A | Primary tumor | 0.07 | 0.12 | 0.03 | 0.03 | 0.04 | 0.06 | 0.22 | 0.15 | 0.22 | 0.25 | 0.06 | 0.00 |
| C0153H | Normal mucosa | 0.33 | 0.24 | 0.13 | 0.09 | 0.15 | 0.15 | 0.10 | 0.07 | 0.27 | 0.23 | 0.18 | 0.00 |
| C0353H | Normal mucosa | 0.05 | 0.03 | 0.04 | 0.01 | 0.03 | 0.03 | 0.20 | 0.15 | 0.35 | 0.26 | 0.03 | 0.00 |
| C0297H | Normal mucosa | 0.46 | 0.44 | 0.42 | 0.38 | 0.45 | 0.45 | 0.47 | 0.37 | 0.45 | 0.41 | 0.43 | 1.00 |
| C0667H | Normal mucosa | 0.17 | 0.30 | 0.04 | 0.09 | 0.06 | 0.07 | 0.49 | 0.39 | 0.44 | 0.43 | 0.12 | 0.00 |
| C0353U | Liver met | 0.07 | 0.05 | 0.00 | 0.02 | 0.02 | 0.05 | 0.26 | 0.43 | 0.46 | 0.47 | 0.04 | 0.00 |
| C0329U | Liver met | 0.04 | 0.03 | 0.01 | 0.00 | 0.02 | 0.02 | 0.21 | 0.29 | 0.39 | 0.47 | 0.02 | 0.00 |
| 12051V | Lung met | 0.03 | 0.02 | 0.00 | 0.00 | 0.02 | 0.06 | 0.55 | 0.46 | 0.50 | 0.50 | 0.02 | 0.00 |

Figure 16

| CRC Type | Tissue | LRAT methylation |
|---|---|---|
| MSI (Paty 3 markers) | (n=40) | 37/40 (92.5%) |
| Non-MSI | Polyps (n=13) | 12/13 (92.3%) |
| | Stage I (n=15) | 10/15 (66.7%) |
| | Stage II (n=15) | 10/15 (66.7%) |
| | Stage III (n=21) | 7/21 (33.3%) |
| | Stage IV (n=29) | 12/29 (41.4%) |
| Metastasis | Liver (n=14) | 5/14 (35.7%) |
| | Lung (n=12) | 6/12 (50%) |
| Normal | Colon musoca (n=69) | 12/69 (17.4%) |

Figure 17

Stage I+II+III+IV disease specific survival analysis

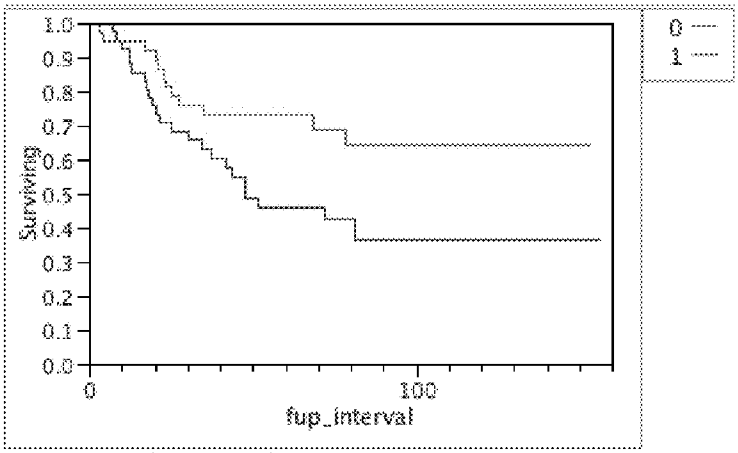

Time to event: fup_interval
Censored by (5 yr Dis Specific)Censor
Grouped by Methyl score

Summary

| Group | N Failed | N Censored | Mean | Std Error |
|---|---|---|---|---|
| 0 | 23 | 19 | 51.3618 Biased | 4.72049 |
| 1 | 12 | 27 | 62.2821 Biased | 4.4991 |
| Combined | 35 | 46 | 57.5843 Biased | 3.35108 |

Quantiles

| Group | Median Time | Lower95% | Upper95% | 25% Failures | 75% Failures |
|---|---|---|---|---|---|
| 0 | 47.5 | 30 | . | 20.2 | . |
| 1 | . | 78.46 | . | 34.5 | . |
| Combined | . | 47.5 | . | 24.67 | . |

Tests Between Groups

| Test | ChiSquare | DF | Prob>ChiSq |
|---|---|---|---|
| Log-Rank | 4.7315 | 1 | 0.0296 |
| Wilcoxon | 3.8685 | 1 | 0.0492 |

Figure 18

Stage II+III disease specific survival analysis

Time to event: fup_interval
Censored by (5 yr Dis Specific)Censor
Grouped by Methyl score

Summary

| Group | N Failed | N Censored | Mean | Std Error |
|---|---|---|---|---|
| 0 | 6 | 13 | 69.4912 Biased | 5.39296 |
| 1 | 1 | 16 | 27.1 Biased | . |
| Combined | 7 | 29 | 73.7839 Biased | 3.26433 |

Quantiles

| Group | Median Time | Lower95% | Upper95% | 25% Failures | 75% Failures |
|---|---|---|---|---|---|
| 0 | 81.3 | 51.3 | . | 51.3 | . |
| 1 | . | . | . | . | . |
| Combined | . | 81.3 | . | 81.3 | . |

Tests Between Groups

| Test | ChiSquare | DF | Prob>ChiSq |
|---|---|---|---|
| Log-Rank | 4.4459 | 1 | 0.0350 |
| Wilcoxon | 3.0696 | 1 | 0.0798 |

USE OF LECITHIN:RETINOL ACYL TRANSFERASE GENE PROMOTER METHYLATION IN EVALUATING THE CANCER STATE OF SUBJECT

This application claims the benefit of U.S. Provisional Patent Application Ser. No. 60/870,765 filed Dec. 19, 2006, which is hereby incorporated by reference in its entirety.

The subject matter of this application was made with support from the United States Government under the National Cancer Institute, Grant Nos. P30 CA29502 and P01-CA65930. The U.S. Government has certain rights.

FIELD OF THE INVENTION

The present invention relates to the use of lecithin:retinol acyl transferase (LRAT) gene promoter methylation in cancer diagnosis and prognosis.

BACKGROUND OF THE INVENTION

Cancers contain altered methylation patterns that result in aberrant expression of critical genes. Hypermethylation turns off the expression of genes required to regulate normal growth, while hypomethylation allows the inappropriate expression of genes that permit cellular proliferation. Aberrant promoter hypermethylation occurs at the 5-prime position of cytosine within a CpG dinucleotide (Gardiner-Garden et al., *J. Mol. Biol.* 196(2): 261-82 (1987)). It inactivates the expression of critical genes that are involved in tumor suppression, DNA repair, control of tumor metastasis and invasion (Feinberg et al., *Nature.* 301: 89-92 (1983); Jones et al., *Nat. Rev. Genet.* 3(6): 415-28 (2002)). In colorectal cancer (CRC), for example, epigenetic silencing of O(6)-methylguanine-DNA methyltransferase is associated with G to A mutations in K-ras and p53 genes (Esteller et al., *Cancer Research* 61(12):4689-92 (2001); Esteller et al., *Cancer Research* 60(9):2368-71 (2001)). Hypermethylation of the mismatch repair gene, hMLH1, is linked to a sporadic microsatellite instability phenotype in colon tumors (Herman et al., *Proc Natl Acad Sci USA.* 95(12):6870-6875 (1998); Kane et al., *Cancer Res.* 57(5):808-811 (1997)). Furthermore, the hypermethylated $p16^{INK4a}$ and $p14^{ARF}$ reside in a genomic region (9p21) that commonly undergoes loss of heterozygosity, suggesting that methylation silencing may cooperate with other genetic alterations for gene inactivation (Weber et al., *Cytogenet Cell Genet.* 86(2):142-147 (1999)).

Retinoids, a class of natural and synthetic vitamin A analogues, are important therapeutic agents used in oncology and hematology (Altucci et al., *Nat Rev Cancer* 1(3):181-193 (2001); Niles R. M., *Mutat Res.* 555(1-2):81-96 (2004)). Retinoids are metabolized into two main classes of biologically active compounds, retinal and retinoic acid (RA). Retinal is essential for the formation of rhodopsin the visual chromophore, while RA serves as an important factor in regulating the expression of a large number of genes, primarily by functioning as a ligand activator for two families of nuclear retinoid receptors: retinoic acid receptors (RARs) and retinoid X receptors (RXRs) (Altucci et al., *Trends Endocrinol Metab.* 12(10):460-468 (2001); Kastner et al., *Development.* 124(2):313-326 (1997); Mangelsdorf et al., *Cell* 83(6):835-839 (1995)). Adequacy of vitamin A and its metabolites have been linked to the occurrence of various human cancers (Crowe et al., *Mol Cancer Res.* 1(7):532-540 (2003); Hayden et al., *Breast Cancer Res Treat.* 72(2):95-105 (2002); Mahmoud et al., *Int J Cancer.* 30(2):143-145 (1982)). In CRC, aberrant crypt foci (ACF) are proposed to be preneoplastic lesions occurring in hyperproliferative human colon tissues and carcinogen-treated laboratory animals. The formation of carcinogen-induced ACF can be inhibited by retinol, 9-cis-RA, and 4-(hydroxyphenyl)retinamide in animal models (Wargovich et al., *Carcinogenesis.* 21(6):1149-1155 (2000); Zheng et al., *Carcinogenesis* 20(2):255-260 (1999)). In vitro matrigel and in vivo xenograft models of CRC treated with trans-RA, 9-cis-RA and 13-cis-RA show reduced MMP7 expression and proteolytic degradation of the extracellular matrix, important mechanisms of tumor invasion (Adachi et al., *Tumour Biol.* 22(4):247-253 (2002)). In addition, several in vitro studies indicate that retinoids have potent antiproliferative effects on CRC cell lines and may have chemopreventive and chemotherapeutic potential for CRC (Briviba et al. *Biol Chem.* 382(12):1663-1668 (2001); Callari et al., *Int J Oncol.* 23(1):181-188 (2003); Park et al., *Cancer Res.* 65(21):9923-9933 (2005)). The association between retinoid levels and cancer development suggests that retinoids offer great promise for cancer therapies and most studies have focused on the retinoid signaling pathways in suppressing carcinogenesis. Although the key players of retinoid biosynthesis have been identified, the mechanism of regulating the cellular RA concentration is not well understood, but is critically related to tumor development.

Retinoids are metabolized via sequential oxidation steps (shown in FIG. 1). The key molecules involved in the metabolism consist of a family of retinol dehydrogenases (RDHs), several class I aldehyde (retinal) dehydrogenases (ALDHs/RALDHs), a family of chaperone-like regulatory proteins the cellular retinol-binding proteins (CRBPs) and the cellular retinoic acid binding proteins (CRABPs) (Sophos et al., *Chem Biol Interact.* 143-144:5-22 (2003); Yoshida et al., *Eur J Biochem.* 251(3):549-557 (1998); Wei et al., *Dev Dyn.* 201(1):1-10 (1994); Ong et al., *Biochim Biophys Acta.* 1482 (1-2):209-217 (2000); Vogel et al., *J Biol Chem.* 276(2):1353-1360 (2001)). Furthermore, a plausible mechanism has been proposed that two "gate-keeping" molecules, lecithin:retinol acyl transferase (LRAT) and cytochrome P450 enzymes (CYP26s), are coordinately regulated by all-trans RA to control the availability of retinol and RA, respectively (Ross, *J Nutr.* 133(1):291S-296S (2003)). The synthesis of retinyl esters (RE), the principal cellular storage form of retinol in the stellate cells of the liver, is catalyzed by LRAT and a less characterized enzyme acyl CoA:retinol acyltransferase (ARAT) (Guo et al., *Carcinogenesis* 21(11):1925-1933 (2000)). Genetic studies have shown that CYP26s convert RA to less active and more readily excretable polar metabolites. A deficiency of retinoic acid biosynthetic enzymes in colon epithelial tissues has been proposed to lead to decreased mucus production, expansion of proliferation zones within the crypt, ion flux alterations, and development of premalignant and malignant cells during tumorigenesis (Jette et al., *J Biol Chem.* 279(33):34397-34405 (2004)). Understanding these regulating factors may facilitate the use of dietary or pharmacological means for the prevention and improved treatment of human cancer.

The present invention is directed to overcoming these and other deficiencies in the art.

SUMMARY OF THE INVENTION

One aspect of the present invention is directed to a method of evaluating the cancer state of a subject. The method includes isolating a sample of DNA from the subject and determining a first methylation level of the LRAT gene promoter nucleotide sequence, or the region upstream of the LRAT gene promoter nucleotide sequence, in the sample. The detection of a methylated LRAT gene promoter nucleotide sequence, or region upstream thereof, within the sample, permits evaluation of the cancer state of the subject.

A second aspect of the present invention relates to a method of determining the prognosis of a subject having cancer. This method includes assessing the level of LRAT mRNA expression in a sample obtained from the subject and comparing the level of LRAT mRNA expression in the sample to the level of LRAT mRNA expression in a reference RNA standard. A decrease in LRAT mRNA expression in the sample compared to the reference standard indicates a favorable prognosis for the subject A third aspect of the present invention relates to a method of determining the prognosis of a subject having cancer. This method includes assessing the level of LRAT protein expression in a sample obtained from the subject and comparing the level of LRAT protein expression in the sample to the level of LRAT protein expression in a reference protein standard. A decrease in LRAT protein expression in the sample compared to the reference standard indicates a favorable prognosis for the subject A fourth aspect of the present invention relates to a method of treating a subject for cancer. The method includes treating a subject with a pharmaceutical composition which inhibits LRAT activity under conditions effective to treat said cancer.

The basis for the present invention is applicants' discovery that there is an association between CRC carcinogenesis and LRAT genetic and epigenetic alteration. In particular, it is believed the LRAT promoter methylation status has indicative value in cancer prevention and treatment. Recent studies have shown reduced LRAT activity in tumor cell lines and tissues of prostate, breast, oral cavity, and skin cancers (Boorjian et al., *Clin Cancer Res.* 10(10):3429-3437 (2004); Guo et al., *Cancer Res.* 62(6):1654-1661 (2002); Guo et al., *Carcinogenesis.* 21(11):1925-1933 (2000) which are hereby incorporated by reference in their entirety). Based on these observations, applicants believe that deficiency of retinyl ester synthesis may be correlated with tumor development or early stages of tumorigenesis. The aberrant promoter hypermethylation of LRAT may contribute to the reduced LRAT activity or gene silencing resulting in the deficiency of retinyl ester synthesis. The profiling of LRAT promoter methylation status, in conjunction with other molecular markers and clinicopathological information may provide a more precise "molecular signature" of disease for accurate diagnosis and prognosis.

BRIEF DESCRIPTION OF THE DRAWINGS

FIG. 2 is a schematic diagram, illustrating the procedure for high-throughput detection of promoter methylation status with the combination of bisulfite treatment, multiplex PCR, multiplex LDR, and universal array approaches. The different fluorescently labeled (Cy3 and Cy5) LDR products are captured on the same addressable array.

FIG. 4 is a schematic diagram, illustrating the procedure for high-throughput detection of promoter methylation status with the combination of bisulfite treatment, multiplex PCR, multiplex LDR, and universal array approaches. The different fluorescently labeled (Cy3 and Cy5) LDR products are captured on separate addressable arrays.

FIG. 5 is a schematic diagram, illustrating the procedure for high-throughput detection of promoter methylation status with the combination of bisulfite treatment, multiplex PCR, multiplex LDR, and universal array approaches. Nucleotide analogs dK and dP are introduced in the multiplex PCR primer and LDR probe designs (at methylation sites 1, 3, 7, and 8). These analog-containing oligonucleotide primer/probes have the capability of hybridizing to DNA sequences regardless of whether the templates are fully, partially, or un-methylated.

FIG. 6 is a schematic diagram, illustrating the procedure for high-throughput detection of promoter methylation status with the combination of bisulfite treatment, multiplex PCR, multiplex LDR, and capillary electrophoresis approaches. Nucleotide analogs dK and dP are introduced in the multiplex PCR primer and LDR probe designs (at methylation sites 1, 3, 7, and 8). These analog-containing oligonucleotide primers/probes have the capability of hybridizing to DNA sequences regardless whether the templates are fully or partially methylated.

FIG. 7 is a schematic diagram, illustrating the procedure for high-throughput detection of promoter methylation status with the combination of bisulfite treatment, multiplex PCR, multiplex LDR, and universal array approaches. Nucleotides G and C are used in the multiplex PCR primers and LDR probes. The hybridization of such primers/probes with their DNA template results in the C:G Watson-Crick base pairings on methylated genomic sequences, yet G:T wobble base pairings and C:A mismatches occur on un-methylated sequences. Thus, the designs of these primers/probes take advantage of preferentially hybridizing to methylated DNA sequences. As shown in this diagram, for example, the methylation sites 1, 3, 7, and 8 contribute to the preferential enrichment of the final signal of methylated cytosines at methylation sites 2 and 6.

FIG. 12A is the promoter sequence of LRAT (SEQ ID NO:1). Matching bases in coding regions of cDNA and genomic sequences are capitalized (bases 297-835). Matching bases in UTR regions of cDNA and genomic sequences are in italics (bases 102-191). Underlined bases mark the boundaries of gaps, often splice sites in the coding sequence (bases 296 and 836) or the UTR sequence (bases 101, 108, and 192). All CpG dinucleotides are in bold and the interrogated cytosines are double underlined.

FIG. 16 shows a typical quantitative analysis of CpG methylation levels in LRAT promoter regions. Ten CpG dinucleotides were analyzed. CpG sites 1-6 are located in the 5'-UTR and CpG sites 7-10 are located in exon-1. The methylation levels of CpG sites 1-6 were averaged and used to score the overall LRAT promoter methylation status. An average methylation level of >0.2 was considered as hypermethylated whereas a level of ≤0.2 was considered unmethylated.

FIG. 17 is a summary of LRAT promoter methylation status in all CRC tumor samples analyzed (n=131). Tumor samples were grouped into two subtypes based on their Microsatellite Instability (MSI) status. In the non-MSI category, tumor samples were further classified based on their clinicopathological stage (polyps, stage I, stage II, stage III, and stage IV). The percentage of LRAT promoter methylation in each sub-group is indicated. A decreasing methylation percentage is associated with the advancing of tumor stage.

FIG. 18 shows the disease specific Kaplan-Meier survival analysis. CRC tumor samples of all four clinical stages were included in the survival analysis. Data were stratified by Bisulfite/PCR-PCR/LDR/Universal Array assay. The Log-Rank test shows a Chi-Square=4.73 and P=0.0296.

DETAILED DESCRIPTION OF THE INVENTION

Figure 1:
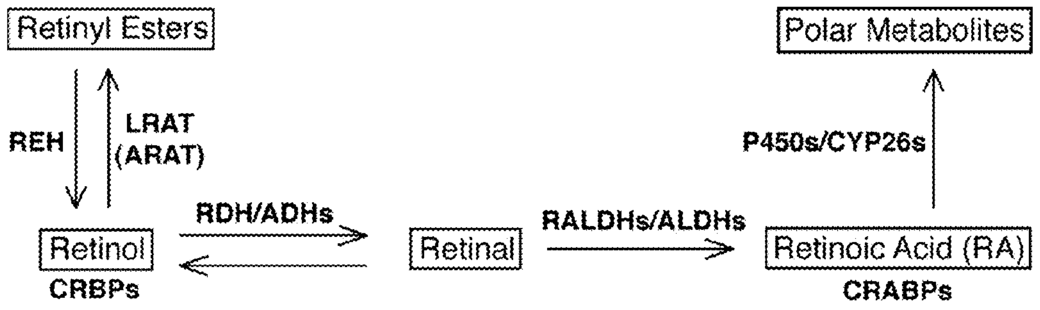
FIG. 1 is a schematic diagram of enzymes and protein factors involve in retinol metabolism.
Figure 3:
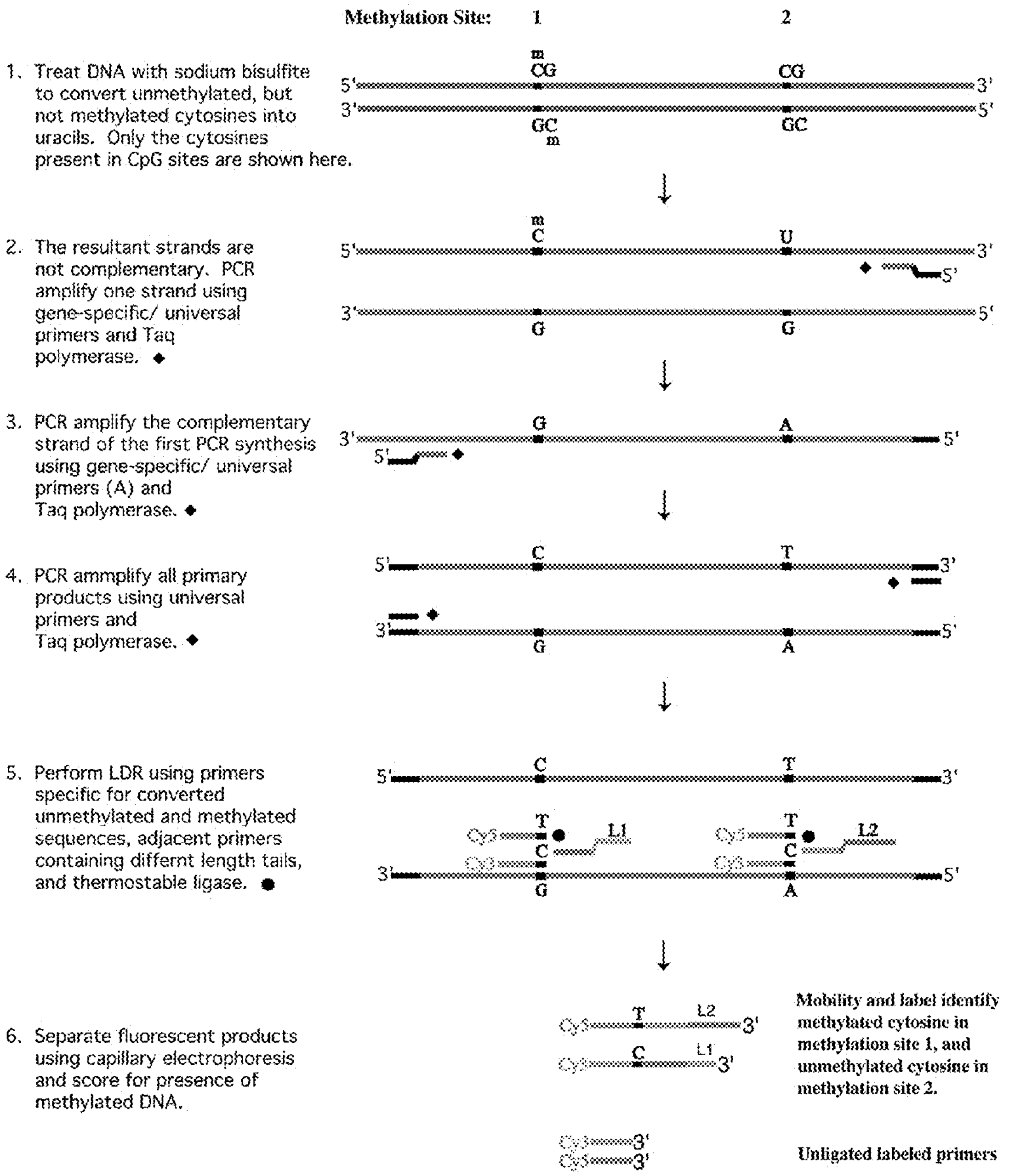
FIG. 3 is a schematic diagram, illustrating the procedure for high-throughput detection of promoter methylation status with the combination of bisulfite treatment, multiplex PCR, multiplex LDR, and capillary electrophoresis approaches. The fluorescent labeled (Cy3 and Cy5) LDR products are separated using capillary electrophoresis and scored for presence of methylated DNA.
Figure 8:
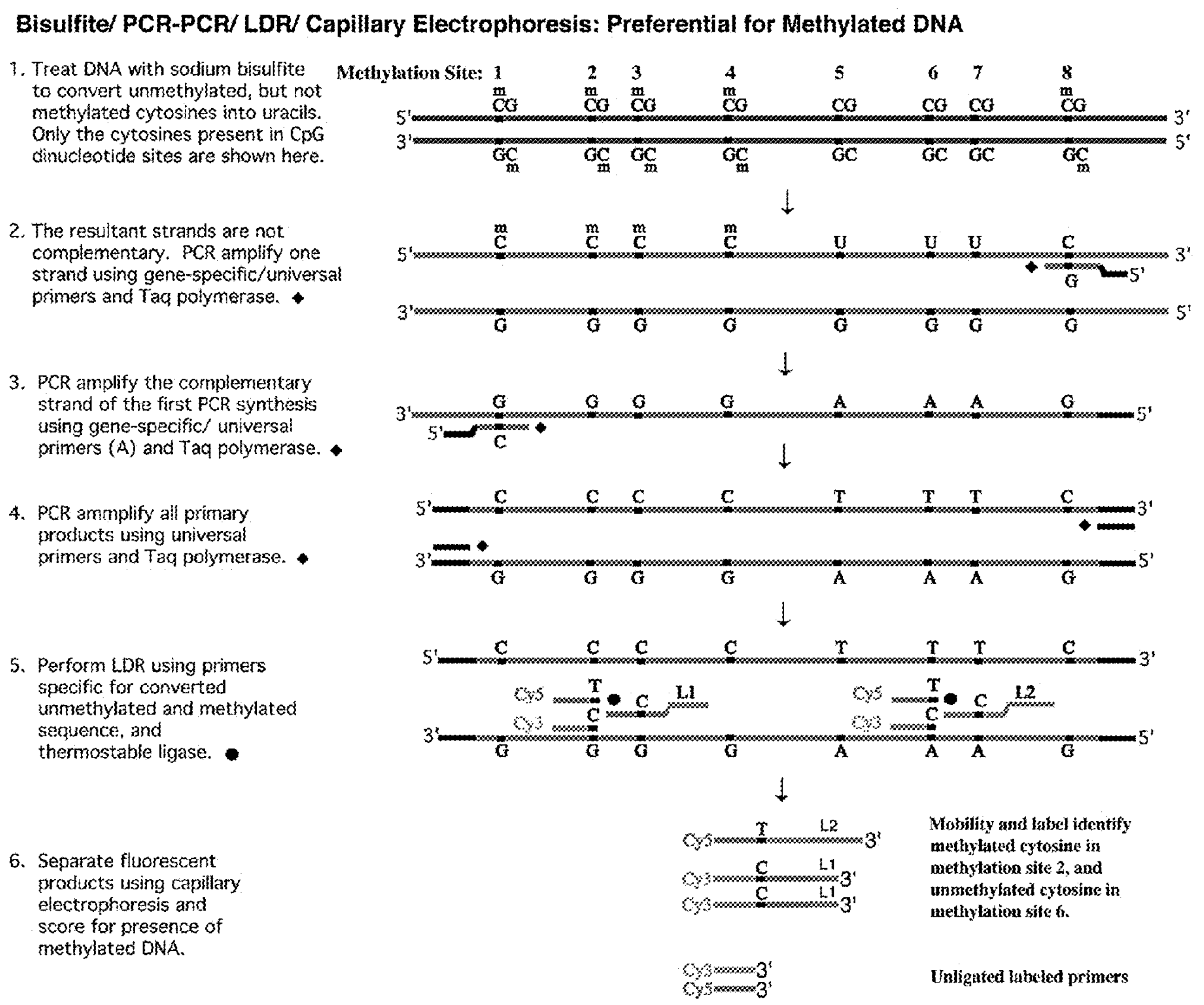
FIG. 8 is a schematic diagram, illustrating the procedure for high-throughput detection of promoter methylation status with the combination of bisulfite treatment, multiplex PCR, multiplex LDR, and capillary electrophoresis approaches. Nucleotides G and C are used in the multiplex PCR primers and LDR probes. The hybridization of such primers/probes with their DNA template results in the C:G Watson-Crick base pairings on methylated sequences, yet G:T wobble base pairings and C:A mismatches occur on un-methylated sequences. Thus, the designs of these primers/probes take advantage of preferentially hybridizing to methylated DNA sequences. As shown in this diagram, for example, the methylation sites 1, 3, 7, and 8 contribute to the preferential enrichment of the final signal of methylated cytosines at methylation sites 2 and 6.

One aspect of the present invention is directed to a method of evaluating the cancer state of a subject. The method includes isolating a sample of DNA from the subject and determining a first methylation level of the LRAT gene promoter nucleotide sequence, or the region upstream of the LRAT gene promoter nucleotide sequence, in the sample. The detection of a methylated LRAT gene promoter nucleotide sequence, or region upstream thereof, within the sample, permits evaluation of the cancer state of the subject.

A preferred embodiment of the method of the present invention can further include comparing the first methylation level of the LRAT gene promoter nucleotide sequence, or region upstream thereof, to a second methylation level of a LRAT gene promoter nucleotide sequence, or region upstream thereof, in a reference DNA sample. A difference between the first and second levels of the LRAT promoter methylation also permits evaluation of the cancer state of the subject.

Evaluation of a cancer state as described herein can include cancer detection, cancer diagnosis, and cancer prognosis. Evaluation of a cancer state can also include monitoring cancer progression.

Cancer detection as described herein refers to the initial finding or discovery of cancerous or pre-cancerous tissue. For example, cancer detection can include the early detection of a polyp or adenoma, which are usually benign but may turn cancerous over time.

Cancer diagnosis as described herein refers to determining the nature of the cancer state, i.e. the clinical stage of a cancer associated with its progression or the specific phenotype of a cancer or tumor.

Cancer prognosis as described herein includes determining the probable course and outcome of the cancer and can include determining the chances of recovery and survival of a subject with the cancer. A favorable prognosis refers to an increased probability of recovery and/or survival for the patient having cancer.

Cancer progression in a subject is monitored by comparing the methylation level of the LRAT gene promoter in one or more tissue samples obtained from the subject at multiple time points. A change in the methylation level over time indicates a change in the status of the cancer.

The cancer state to be evaluated by the present invention can be any cancer in which methylation of the LRAT promoter sequence, or region upstream thereof, is altered. Examples of cancers to be evaluated using the method of this invention include, but are not limited to, colorectal cancer (CRC), prostate cancer, renal cancer, pancreatic cancer, breast cancer, skin cancer, oral cavity cancer, lung cancer, gastrointestinal cancer, liver cancer, head and neck cancer, and brain cancer.

In one embodiment of the present invention, the methylation level of the LRAT gene promoter sequence, or region upstream thereof, is determined by measuring the level of methylation at one or more defined CpG nucleotide sites within the promoter nucleotide sequence, or region upstream thereof. In a sample containing one or more of a plurality of target LRAT gene promoter nucleotide sequences, or regions upstream thereof, this methylation level can be quantified. This method of quantification comprises measuring the total number of CpG nucleotide sites within the sample and comparing the number of methylated CpG nucleotides at a defined site with the number of unmethylated CpG nucleotides at the corresponding defined site. The ratio of site specific methylated CpG nucleotides to the sum of the site specific methylated and unmethylated CpG nucleotides provides a quantitative measure of the methylation level at a defined CpG nucleotide site in the sample. The detection of methylation at one or more defined CpG nucleotide sites within the LRAT promoter nucleotide sequence, or region upstream thereof, in a DNA sample indicates the presence of cancer. The detection of methylation also has cancer diagnostic and prognostic value. A difference in the level of methylation at one or more defined CpG nucleotide sites within the LRAT promoter nucleotide sequence, or region upstream thereof, in a DNA sample compared to the level of methylation at corresponding CpG nucleotide sites within a LRAT promoter nucleotide sequence, or region upstream thereof, in a reference sample is also indicative of the presence of cancer within the sample. Likewise, a difference in the level of methylation at one or more defined CpG nucleotide sites within the LRAT promoter nucleotide sequence, or region upstream thereof, in a DNA sample compared to a reference sample has cancer diagnostic and prognostic value. Additionally, the specific pattern of methylation at one or more defined CpG nucleotide sites within the LRAT promoter nucleotide sequence, or upstream region thereof, also has diagnostic and prognostic value.

In a second embodiment of the present invention, the methylation level of the LRAT gene promoter sequence, or region upstream thereof, is determined by measuring the overall level of methylation across various CpG sites within the LRAT promoter nucleotide sequence, or region upstream thereof. In a sample containing one or more of a plurality of target LRAT gene promoter nucleotide sequences, or regions upstream thereof, this methylation level is quantified by first determining the level of methylation at individual CpG sites within the LRAT promoter nucleotide sequence, or region up stream thereof. Next, the average level of methylation across individual CpG sites is calculated. This average indicates the overall level of methylation in the LRAT promoter nucleotide sequence, or region upstream thereof. The detection of methylation within the LRAT gene promoter, or region upstream thereof, indicates the presence of cancer. A difference in the overall level of methylation within the LRAT gene promoter sequence, or region upstream thereof, in a DNA sample compared to the overall level of methylation within a LRAT gene promoter sequence, or region upstream thereof, in a reference DNA sample indicates the presence of cancer. Likewise, a difference in the overall level of methylation in the LRAT gene promoter sequence, or region upstream thereof, in a DNA sample compared to a reference sample has cancer diagnostic and prognostic value as described above.

The LRAT gene promoter nucleotide sequence comprises SEQ ID NO:1 as follows:

```
gcccccaggt gcgctccttc tccggctgct tgtagcactg gtctcactgt ccccgccgtc    60
agccaccggt tccttatccg tctcattccc cattgtggct tggctgagcc ggtcgccagg   120
cctcgctgtc ctcctttgcc ttcctctctc ctcagcggcc gtactttgcg ccgtacctca   180
cctggcctgc aggtgagcag cagcgcagca cccctgcccg gcgagcttaa cttgcccagc   240
ccggcccctg ccggagtggc accggcacct ctccaagacg ccctcttccc tgcaggatga   300
agaaccccat gctggaggtg gtgtctttac tactggagaa gctgctcctc atctccaact   360
tcacgctctt tagttcgggc gccgcgggcg aagacaaagg gaggaacagt ttttatgaaa   420
ccagctcttt ccaccgaggc gacgtgctgg aggtgccccg gacccacctg acccactatg   480
gcatctacct aggagacaac cgtgttgccc acatgatgcc cgacatcctg ttggccctga   540
cagacgacat ggggcgcacg cagaaggtgg tctccaacaa gcgtctcatc ctgggcgtta   600
ttgtcaaagt ggccagcatc cgcgtggaca cagtggagga cttcgcctac ggagctaaca   660
tcctggtcaa tcacctggac gagtccctcc agaaaaaggc actgctcaac gaggaggtgg   720
```

-continued

```
cgcggagggc tgaaaagctg ctgggcttta ccccctacag cctgctgtgg aacaactgcg   780

agcacttcgt gacctactgc agatatggca ccccgatcag tccccagtcc gacaaggtat   840

gatgtgtgac tcccagggga agtgggctcc gcggagatgc cccctcccat ccctgacctt   900

ttctcttccc cgcgagtagg gatctaattc ctggacacct cccctaccac              950
```

The methylation level of the LRAT gene promoter nucleotide sequence is determined by analysis of one or more of the CpG nucleotide sites in SEQ ID NO:1 or a combination thereof. The methylation level of the LRAT gene promoter nucleotide sequence can be determined at nucleotides 12, 23, 54, 57, 67, 79, 110, 114, 124, 156, 160, 169, 172, 204, 219, 222, 242, 252, 263, 279, 364, 376, 380, 383, 385, 389, 435, 440, 443, 459, 501, 521, 545, 555, 559, 582, 596, 621, 623, 644, 650, 680, 710, 721, 723, 779, 788, 814, 830, or a combination thereof, in SEQ ID NO:1.

LRAT methylation analysis can also include examination of CpG nucleotides in the region (SEQ ID NO:2) upstream of the promoter. SEQ ID NO:2 is as follows:

```
agtttagaaa accaaatttc tcaggcctag agctcaagta aaagaaaatc tgagataatg     60

aagtctggaa cactgggcct gcattctgct cctgactctg tgcccttggg taagacattg    120

aacttcccca ccccagattc atcctacacc ctaaggaggg tgtaggattt tgtagccttc    180

ctagtgatgg catactatta atcagaacct taaccagctc tattctcact atcccagtaa    240

aatgatgtta aaaattagac ctcgtgacat gagagaagag gggaaattaa ttacagatta    300

caaagaaatt gtgggatcta agtttagggt gaggtgtttt attgaacctc tagggttggt    360

catagcacct gccatatagc aggtattcaa taaatgatgt gtaatgggtg gttagactga    420

tggaaaggca ggccttccca gtgacggtaa aggacctggg gcaaaagaga cctgtggttg    480

agtcctgatc cccacacatt agcacactga ctagacgaag ttataagctt caatttcttc    540

ctgtgtaaaa tggagataat acctcatagg gttatgagga ttaaataaga aaatgcttag    600

ttcagtgcct aatacacagg aagcacaccg taaatattag ttattattat tactaatact    660

gtgatcatat cttccatcca aagacttctc tgaggagcag gggcatcca gagataaaaa     720

gcctgcaggt gggaaatctg ttagccttct agggcgttag gtttctgtgg aactctgcac    780

ctcttccctg tcctagttct taagaacaga aactctccag ggacctctgg tgaggtagcc    840

gtgggaagat gaggtgcaga agtaagctgg gacctgtgag cctcaatttc ggcctcttct    900

gcgctgagac ccaagcggat cttgcttggc ctgtatgcgt tactggggga aatggacgtg    960

ggcctgagcg cggcaggtgc gagggcgctg ccccggggcc gaccaccctg cggggacact   1020

gtagctgtca ttccttcttc tgcaggcggg taggggaagc ggtggccaaa gtgggagtcg   1080

accgctcagc acagtctgtc tgagtgttga ccaggaaagt ccaggctctt tctaaatctc   1140

gccgccagac ctggtgacgc attcgcatgt atttaaggcg tttgcacgca gaacgttatc   1200

acagaatgta gccacctttc ttaacggtcc gggaaaccag aggtctctcc agctactcag   1260

ggtagaggaa tttctcctat ctccatgtga catcttctga tttagaagaa ctaatgttag   1320

atttctcttg ggcctttcca cctacagcta tagtcttccc tttgtttagc taaaattgag   1380

gcaggtagga aaatattatt gggggcataa gcctattagt gtgtaaacgt atttttatga   1440

agtgtgcctc cagggagcca ttaaaaactg acctctcaac cacagaaata gatgagattt   1500

tgagaacatt gagaagctgc cttttgcaaa gtaaatttgc aatggtcctt gacgaagggg   1560

ggtcgggggc ggggagaagt ccagccgaga gaggagctca ttccacgcta tatttttgca   1620

gttgaaaagc tgcctaatca tcgctaaccg cttcccgcat aagagttctg ggaagacttc   1680

agaaacaagg caaatgaaga cttttcactg cctccttcgg gctgtcgctt ccggaagccg   1740

aagtcctagc acgcagagca gcaggagagg gttactttca ggcaattcca ctgagcaaaa   1800
```

-continued

```
taaatcactt aatggcataa cgttctggct taaaaaattg gaatttatca gaggcaaaaa   1860

tatccttcaa gaaactatgg acactccgcg ccctattcat ttccatggca gcagagtatc   1920

tgcatcttga gccacctata cagattcatg cctcgtatcg ctctcacctc ctttcttttt   1980

gaagtaaagc cctttcccaa gaaggcggcc agaaagtgga ccccaccggg ggaaaaagaa   2040

aaatgaaacg caaatcagct tggcactgct tgcgtcttcc aaaacgcggt gggacaaggc   2100

tattgagtct atagctaatt ctttcatgta tataaaatgt atacatatgt atatattttt   2160

atatacataa aagaattcat atatatgtat atagctatgt ggagccctga agcaattctc   2220

catgcttttg tctccctcaa gttccccagg tggaggcagt cataagcatt ataagccgcc   2280

ttagtgacca ccagggacgg aaaccgttaa ttatcacgtt tcctttcatc tccaggggcc   2340

ctttggcccg tgacacaaga ggcttcggta ttggcgcttt cccagaactg gcccagagga   2400

gccagttcag agtgtgaggt cgggtctgca ttgaacgtac acaccgaggt ctatcagact   2460

cccccgattt tagcgaaggg tgctgactgc tgtgctgcta gaggctagca agctccctgt   2520

gcgcagctga tgagtttcag caactcgcca cctgggcgct tttctttaaa ttttgggagt   2580

aaactgggaa aataaaaaaa tctccacgtc cactggctct ctccccttct ccaacttcct   2640

ctttcgactc gtttgtggga gtttttctcct ctttgctggg actataatgt gatgcgcaat   2700

cgtttgtgaa tgaacaaaag tcaccggcaa gcagggagac ggggacagat cgctgacggc   2760

agattgaggg tggcagcaaa ggcccggcct ccaaggataa tggggagccg ttttccctca   2820

cgcctggtct ctatggcccc cttcgtcttc caggtaaaat gaatgttcct tcatccatca   2880

tccgcagagt accctcaggc gtgcgtagaa tctgctgatg aaacctatta gcgccgactg   2940

ggcagctttg tggagccacc cgaggctctc cattgtggcc tttgtctgca gaatttaagc   3000

atttacataa tgcattagca cggaactcag cacccggtgg ggacatcgcg tgccaagcct   3060

ggcgcggcca acgcttcagc ggctccctca cccggcagct ccctaggacc accctcgagg   3120

aggcattgga gtcgggctgc aggcgcacgg gcaaagaact tagcatctca tccaagtact   3180

tcgccttcct tggccgtctc cgggaggtta tgcttaaaaa cataaaaata aaaataaaaa   3240

taaaaataaa gggaggcgga caaagtttcg gtgggtgaac tgaagctggg tccatgtgac   3300

cctgaagccg gagaaataaa cttaacatga atcttgcttt cctggcgggc gttgggaccc   3360

cgccgttttt catgccaacc gttggaagct tcgtactcaa cggccacagg tgcctaggag   3420

cgcagagagg cctcgggttc aaatcaccgg cgcgcaggga ctggactcgc gggtagcgac   3480

ccccccaacc cccccccccc cgccctacac acacaccctc gcgccggctg aaagcatgga   3540

ggattcaggg catttgaaaa aagaggggct gggcgcggtg gctcacgcct gtaatcccag   3600

cggtttggga ggtccagaag ggcggatcac ttgaggtcag gagttcgaga ccagcctggc   3660

caacaccagc ctggccaaca tggtgagacc ccgtgtctac taaaaataca aaaattagcc   3720

aggcgtggtg cctgtaatat cagctacttg ggaggctgag gcacgagaat cgcttgaacc   3780

tgggaggcgg aggttgcagt gagcccagat cgcgccaccg ccctcctgct ctgggtgata   3840

gagcaaggca ctgtctcaaa acaaaacaaa acaaaacgaa agattcggtc aggaaagaat   3900

ctgcaggcat tcgaggcgct cgcactttgc aaagtaaatg caatctcttt attaagccga   3960

agtccctcat atctatcctt ttagaggaag gtggtccaac tcagaaatct ctcccaagag   4020

gactttccac cgaagactac cgcgaagtgc caggaactcg ccccagtccc gacaggtgca   4080

ggacctttcg tgccgccaca ccttgggact ctacctccct aaataggcca cttaaaagcc   4140

agtagtgcaa ccgggatccc gcggcgataa agaatcactg tgcagaaccc tggagctggg   4200

agtcggcccg caccccctccc aaagaaaccg ggatcccgcg tcctccccgc cgctagcgca   4260
```

-continued

```
gcgcgccagc ggcgcccaat cagtgagctt tccgggtctg tgacggcctt cggctccgcc    4320

ccctcgacgg ccataaaaag tcgcagcgaa gcctgcacct ccgagcaccg cgcgcggccc    4380

tgcccccggc acg                                                        4393
```

Figure 12B:
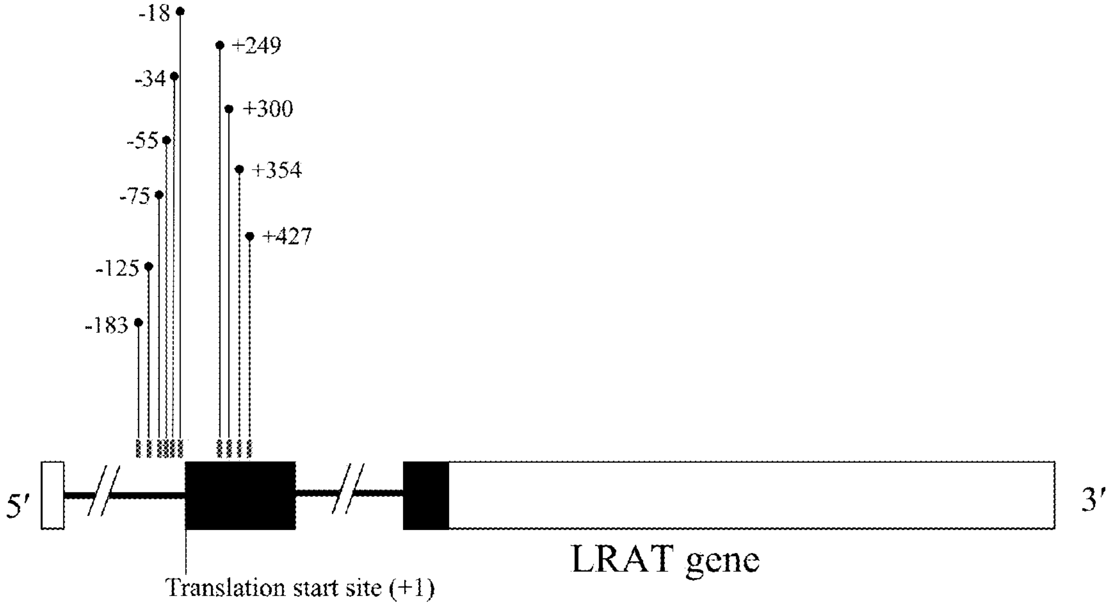
FIG. 12B depicts the position of the interrogated CpG sites within the context of the LRAT gene (bold vertical lines). The positions of the cytosines are indicated relative to the translational start site in the LRAT gene.
Figure 12C:
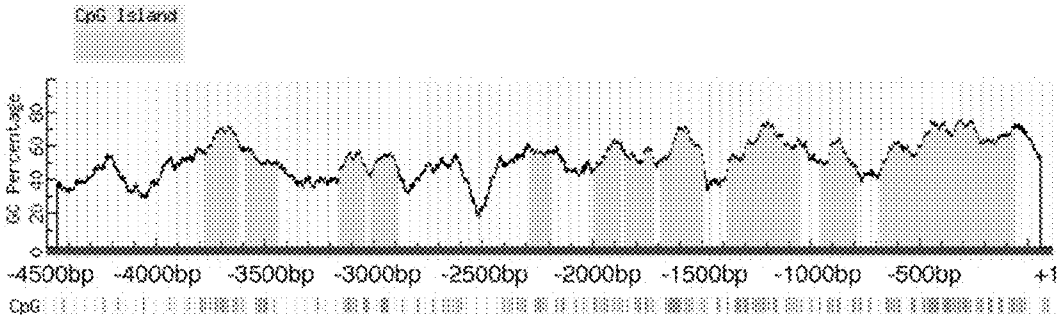
FIG. 12C depicts the CpG nucleotide sites (dark grey bars) within the 4.5 Kb upstream (beginning from the translation start site) LRAT promoter region. The light grey blocks indicate regions of CpG islands.

The 4.5 Kb region upstream of the translation start site of the LRAT gene contains 186 CpG nucleotide sites comprising a number of CpG islands shown in FIG. 12C. The methylation level of the LRAT gene promoter can be determined by analysis of one or more of the CpG sites within SEQ ID NO:2. The methylation level of the LRAT gene promoter can be determined at nucleotides 263, 445, 516, 629, 755, 890, 902, 916, 938, 957, 969, 971, 980, 986, 994, 1000, 1011, 1047, 1060, 1079, 1083, 1140, 1143, 1158, 1164, 1179, 1187, 1194, 1225, 1230, 1428, 1553, 1564, 1570, 1586, 1606, 1642, 1649, 1656, 1718, 1726, 1732, 1739, 1752, 1821, 1887, 1889, 1954; 1959, 2006, 2027, 2049, 2073, 2085, 2087, 2276, 2298, 2305, 2317, 2349, 2366, 2375, 2421, 2436, 2445, 2465, 2474, 2522, 2546, 2557, 2607, 2645, 2650, 2695, 2701, 2725, 2740, 2751, 2757, 2785, 2809, 2821, 2844, 2883, 2900, 2904, 2932, 2935, 2961, 3021, 3035, 3047, 3049, 3063, 3065, 3072, 3080, 3093, 3116, 3133, 3144, 3148, 3182, 3195, 3201, 3257, 3269, 3309, 3346, 3350, 3361, 3364, 3380, 3392, 3401, 3421, 3434, 3448, 3451, 3453, 3468, 3470, 3477, 3501, 3520, 3522, 3525, 3574, 3576, 3586, 3601, 3623, 3646, 3692, 3724, 3764, 3771, 3788, 3811, 3813, 3819, 3877, 3886, 3912, 3917, 3921, 3958, 4031, 4041, 4043, 4059, 4070, 4089, 4094, 4152, 4160, 4162, 4165, 4204, 4209, 4229, 4237, 4239, 4248, 4251, 4257, 4262, 4264, 4270, 4273, 4293, 4304, 4311, 4317, 4325, 4328, 4342, 4347, 4362, 4369, 4371, 4373, 4375, 4387, 4392, or any combination thereof, in SEQ ID NO:2.

The present invention includes determining the methylation level of the LRAT gene promoter nucleotide sequence and the region upstream thereof. This method includes subjecting an isolated DNA sample to a bisulfite treatment to convert unmethylated cytosine residues, but not methylated cytosine residues, into uracil residues. The treatment may be catalyzed by hydroquinone, and may be incubated under cycling conditions to periodically dissociate both strands of genomic DNA to maximize the bisulfite modification efficiency. The method further includes providing one or more primary oligonucleotide primer sets, each set characterized by (a) a first oligonucleotide primer, having a LRAT gene promoter, or region upstream thereof, target-specific portion and a 5' upstream universal primer-specific portion, where the LRAT gene promoter, or region upstream thereof, target-specific portion is suitable for hybridization on a first strand of the LRAT gene in which unmethylated cytosines have been converted to uracil, and (b) a second oligonucleotide primer, having a LRAT gene promoter, or region upstream thereof, target-specific portion and a 5' upstream universal primer-specific portion, where the LRAT gene promoter, or region upstream thereof, target-specific portion is suitable for hybridization on a polymerase extension product of the first strand. A primary polymerase chain reaction mixture comprising the sample, the primary oligonucleotide primer set, and a polymerase, are subjected to two or more polymerase chain reaction cycles. Each cycle comprises a denaturation treatment, where the hybridized nucleic acid sequences are separated, a hybridization treatment, where the target-specific portions of the primary oligonucleotide primer sets hybridize to the target nucleic acid molecules with unmethylated cytosines converted to uracil or to extension products of such modified target nucleic acid molecules, and an extension treatment, where the hybridized primary oligonucleotide primers are extended to form primary extension products complementary to the LRAT gene with unmethylated cytosines converted to uracil. Also provided is a universal oligonucleotide primer set characterized by (a) a first universal primer containing the 5' upstream portion of the first oligonucleotide primer of the primary oligonucleotide primer set, and (b) a second universal primer containing the 5' upstream portion of the second oligonucleotide primer of the primary oligonucleotide primer set. A secondary polymerase chain reaction mixture comprising the primary extension products, the secondary universal oligonucleotide primer set, and the polymerase, is subjected to two or more polymerase chain reaction cycles. Each cycle comprises a denaturation treatment, where the hybridized nucleic acid sequences are separated, a hybridization treatment, where the secondary oligonucleotide primers hybridize to the primary extension products, and an extension treatment, where the hybridized secondary oligonucleotide primers are extended to form secondary extension products complementary to the primary extension products. The method further includes providing a plurality of oligonucleotide probe sets, each set characterized by (a) a first oligonucleotide probe, having a secondary extension product-specific portion and a detectable reporter label, and (b) a second oligonucleotide probe, having a secondary extension product-specific portion and an addressable array specific portion. The oligonucleotide probes in a particular set are suitable for ligation together when hybridized on a complementary secondary extension product, but have a mismatch which interferes with such ligation when hybridized to any other nucleic acid molecule present in the sample. A ligase detection reaction mixture, comprising the secondary extension products, the plurality of oligonucleotide probe sets, and a ligase, is subjected to one or more ligase detection reaction (LDR) cycles. Each cycle comprises a denaturation treatment, where any hybridized oligonucleotides are separated from the secondary extension product, and a hybridization treatment, where the oligonucleotide probe sets hybridize in a base-specific manner to their respective secondary extension products, if present, and ligate to one another to form a ligation product. The oligonucleotide probe sets may hybridize to other nucleic acid molecules but do not ligate together due to a presence of one or more mismatches and individually separate during the denaturation treatment. Ligation products contain (a) the detectable 5'-reporter label and (b) the secondary extension product-specific portions with the addressable array portion connected together. The reporter labels of the ligation products indicate the promoter methylation status of the target LRAT gene promoter nucleotide sequence, or region upstream thereof, in the sample.

A universal array is utilized to capture the ligase detection reaction products. A unique zip-code oligonucleotide sequence has been covalently linked to individual addresses on the universal array. Each address on the universal array can capture a unique ligase detection reaction product by hybridizing to the addressable array-specific portion that is attached to each ligation product. The presence or absence of methyl cytosine can thus be identified based upon the particular fluorescence label attached to the LDR product, and hybridized to a given address on the array. This procedure is described in more detail below and in U.S. Patent Application Publication No. US20050227265 to Barany et al. which is hereby incorporated by reference in its entirety.

A schematic drawing of the methylation analysis process is illustrated in FIGS. 2-10. The initial step of the invention is the preparation of sodium bisulfite modified genomic DNAs. In the preferred embodiment, genomic DNA is incubated with bisulfite and hydroquinone solution for 15-20 hours, more preferably 16 hours, in a DNA thermal cycler (Perkin Elmer Cetus). Suitable cycling conditions involve incubating at 50° C. for 20 minutes, incubating at 85° C. for 15 seconds, and repeating this cycle 45 times. In another embodiment of this process, diethylenetriamine can be used instead of hydroquinone as a catalyst for sodium bisulfite modification (Komiyama et al., *Tetrahedron Letters* 35:8185-8188 (1994), which is hereby incorporated by reference in its entirety). This method comprises a DNA sample potentially containing the methylated as well as native (unmethylated) cytosines in the promoter sequences and sodium bisulfite treatment to convert unmethylated cytosines into uracils. The bisulfite treatment is catalyzed by diethylenetriamine, and the bisulfite solution is pre-equilibrated with argon gas to eliminate the dissolving oxygen before adding the catalyst. The reaction mixture is then incubated under cycling conditions to periodically dissociate both strands of genomic DNA to maximize the bisulfite modification efficiency. Suitable cycling conditions involve incubating at 50° C. for 20 minutes, incubating at 85° C. for 15 seconds, and repeating this cycle 45 times.

The bisulfite treated DNA can be desalted with Wizard DNA clean-up kit (Promega, Madison, Wis.) or, alternatively, it can be desalted using MICROCON centrifugal filter devices (Millipore, Bedford, Mass.). This eliminates bisulfite and fragmented small pieces of nucleic acid molecules while concentrating the treated sample. The desalted DNA is ethanol precipitated, and the DNA pellet is resuspended in deionized $H_2O$ or proper buffer until PCR amplification.

In steps 2 and 3 of the process as shown in FIGS. 2-10, the bisulfite treated genomic DNA is amplified using two PCR primers designed with melting temperatures around 70° C. to hybridize to the complementary sequence of each of the target bisulfite modified sites within the promoter region. Bisulfite modifies DNA asymmetrically, such that the two strands are no longer complementary to each other. Thus, one of the PCR primers has a specific 3' portion that is complementary to DNA that has undergone bisulfite treatment. Since a native cytosine has been converted to a uracil, the PCR primer should have an "A" base opposite the uracil. The resultant PCR primers are usually longer than standard PCR primers since they are now AT rich. When this PCR primer extends across the DNA, the polymerase makes a copy of the uracil containing DNA, incorporating an A opposite T, an A opposite U, a T opposite A, a C opposite G, and a G opposite 5-methyl C as well as residual native C that did not undergo deamination during the bisulfite treatment. The resultant strand is not the same as the opposite strand of bisulfite treated genomic DNA. Consequently, the second PCR primer is designed to be complementary to the extension product of the first bisulfite treated strand of genomic DNA.

A cytosine within a CpG dinucleotide can be converted into uracil (if unmethylated) or remains as cytosine (if methylated) when the target DNA is treated with bisulfite. Nucleotide analogs dK and dP are used in the PCR primers syntheses as depicted in FIGS. 5 and 6 so they will hybridize with similar efficiency to DNA sequences containing bisulfite treated CpG dinucleotides, regardless of whether that initial CpG dinucleotide was fully methylated, partially methylated, or un-methylated. The nucleotide analogues are incorporated in either the PCR primers, the LDR oligonucleotide probes, or both. Those nucleotide positions that specifically base pair to cytosine of CpG dinucleotides are synthesized with the dK analogue. Those nucleotide positions that specifically base pair to the nucleotides complementary to the cytosine of CpG dinucleotides are synthesized with the dP analogue. The pyrimidine derivative dP, when introduced into oligonucleotide primers, base pair with either A or G, while the purine derivative dK base pairs with either C or T. These analog-containing oligonucleotide primers will hybridize with similar efficiency to DNA sequences containing bisulfite-treated CpG dinucleotides, or the complement of such sequence regardless of whether that initial CpG dinucleotide was fully methylated, partially methylated, or un-methylated.

Suitable nucleotide analogues include 2-dimethylaminomethyleneamino-6-methyoxyaminopurine (dK), 6H,8H-3,4-dihydro-pyrimido[4,5-c][1,2]oxazin-7-one (dP), 3-nitropyrrole, 5-nitroindole, and inosine.

Alternatively, those nucleotide positions of primers where dK and dP can be incorporated (see methylation sites 1 and 8 in FIGS. 5-6) are substituted by nucleotides dG and dC, respectively, to make the PCR amplification preferential for methylated alleles. The substituted nucleotide dG in the PCR primer can form either Watson-Crick base pair to C (if it is methylated) or wobble base pair to U (if it is unmethylated) of the bisulfite treated DNA template. The substituted nucleotide dC (at methylation site 1) in the reverse PCR primer can form either Watson-Crick base pair to G (if it is methylated) or mismatch pairing to A (if it is unmethylated) of the extension product of the first PCR primer. Notice that primers designed in this way provide additional selective power for methylated alleles since these positions are located in the middle of oligonucleotide primers.

Figure 9:
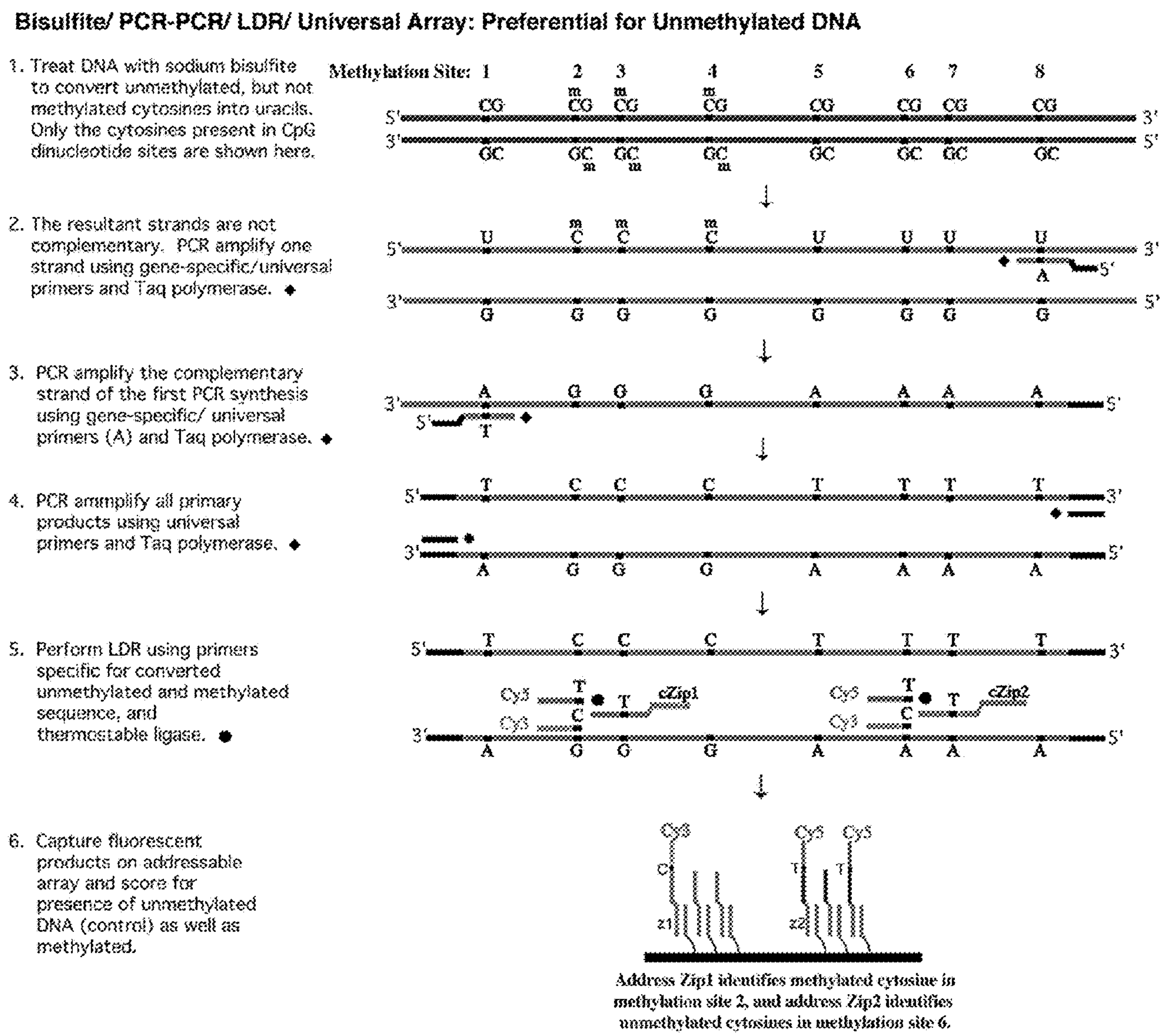
FIG. 9 is a schematic diagram, illustrating the procedure for high-throughput detection of promoter methylation status with the combination of bisulfite treatment, multiplex PCR, multiplex LDR, and universal array approaches. Nucleotides A and T are used in the multiplex PCR primers and LDR probes. The hybridization of such primers/probes with their DNA template results in the A:T Watson-Crick base pairings on un-methylated sequences, yet G:T wobble base pairings of methylated sequences occur. Thus, the designs of these primers/probes take advantage of preferentially hybridizing to un-methylated DNA sequences occur. As shown in this diagram, for example, the methylation sites 1, 3, 7, and 8 contribute to the preferential enrichment of the final signal of un-methylated cytosines at methylation sites 2 and 6.
Figure 10:
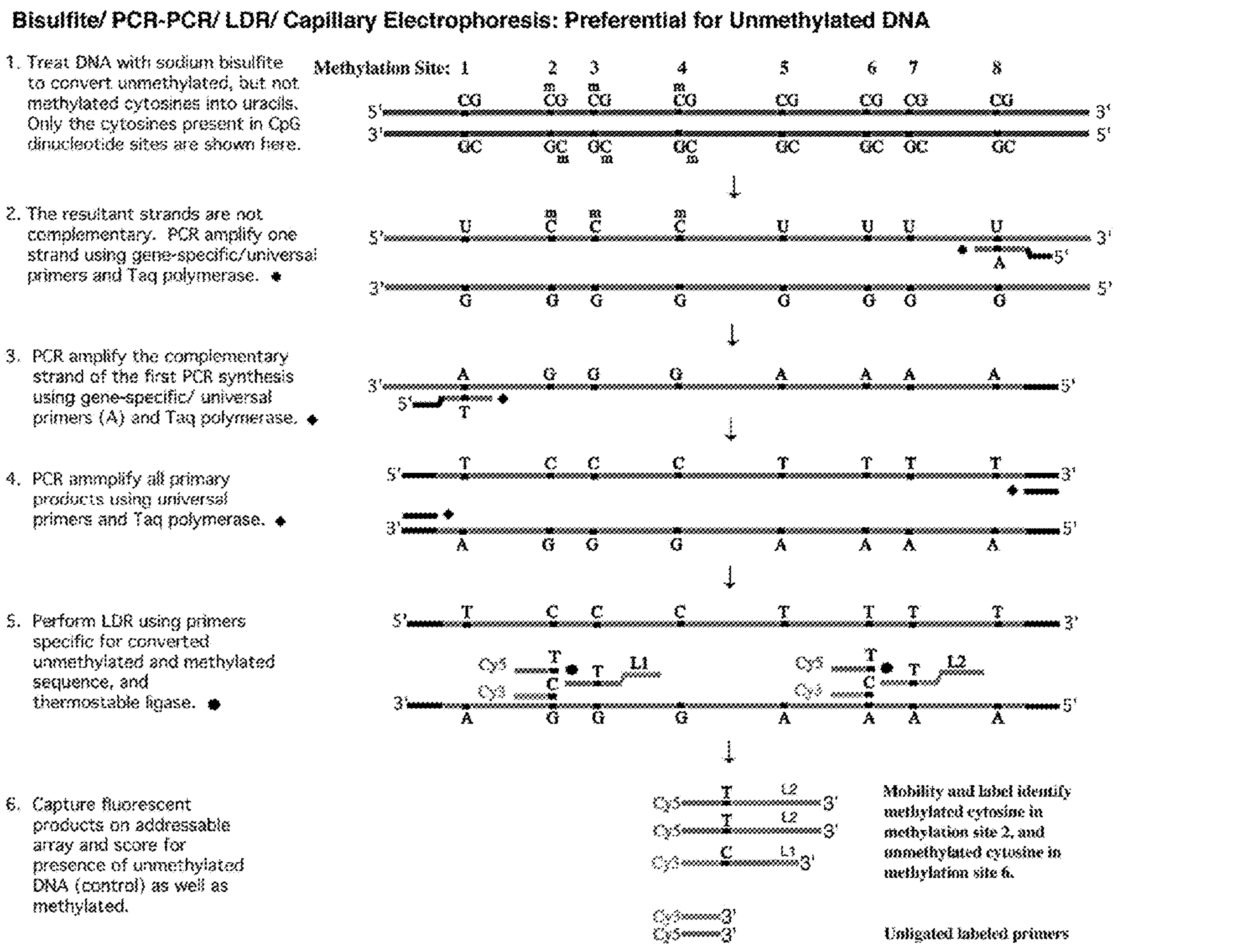
FIG. 10 is a schematic diagram, illustrating the procedure for high-throughput detection of promoter methylation status with the combination of bisulfite treatment, multiplex PCR, multiplex LDR and capillary electrophoresis approaches. Nucleotides A and T are used in the multiplex PCR primers and LDR probes. The hybridization of such primers/probes with their DNA template results in the A:T Watson-Crick base pairings on un-methylated sequences, yet G:T wobble base pairings of methylated sequences occur. Thus, the designs of these primers/probes take advantage of preferentially hybridizing to un-methylated DNA sequences occur. As shown in this diagram, for example, the methylation sites 1, 3, 7, and 8 contribute to the preferential enrichment of the final signal of un-methylated cytosines at methylation sites 2 and 6.
Figure 11:
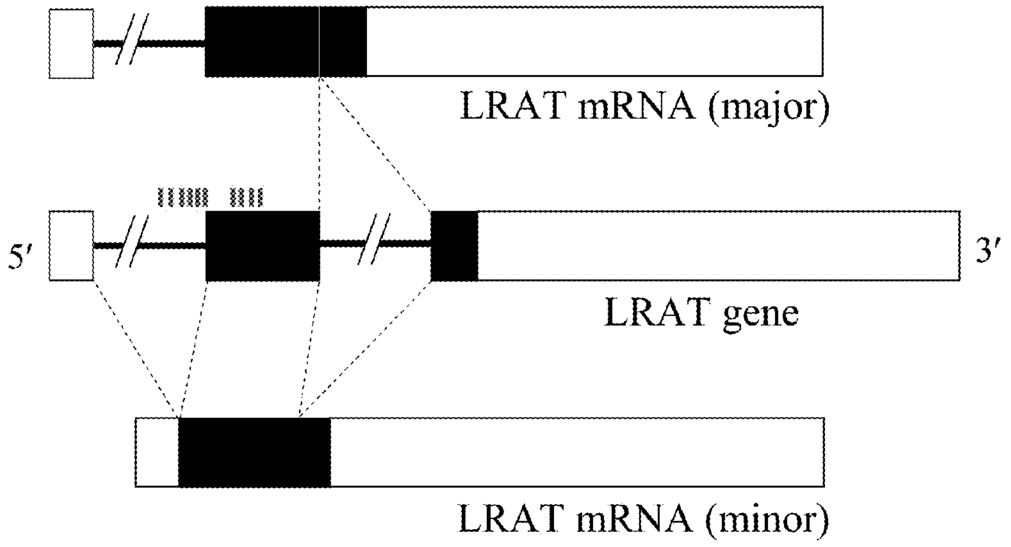
FIG. 11 is a schematic diagram, illustrating the gene structure of LRAT. Two RNA splicing products are illustrated. White and black squares represent untranslated regions (UTRs) and exons, respectively. Black lines represent intronic regions. The location of the ten analyzed CpG sites are illustrated as vertical bars above the LRAT gene structure. Six CpG sites are located within the 5'-UTR and four CpG sites are located in exon-1.

Furthermore, those nucleotide positions of primers where dK and dP can be incorporated (see methylation sites 1 and 8 in FIGS. 5-6) are substituted by nucleotides dA and dT, respectively, to make the PCR amplification preferential for unmethylated alleles. An example of dA is 2'-deoxyAdenosine, and an example of dT is 2'-deoxyThymidine. As shown in FIGS. 9 and 10, the substituted nucleotide dA (at methylation site 8) in the PCR primer can form either a Watson-Crick base pair to U/T (if it is unmethylated) or a mismatch base pair to C (if it is methylated) of the bisulfite-treated DNA template. The substituted nucleotide dT in the reverse PCR primer can form either Watson-Crick base pair to A (if it is unmethylated) or wobble base pair to G (if it is methylated) of the extension product of the first PCR primer. Notice that primers designed in this fashion provide additional selective power for unmethylated alleles since these positions are located in the middle of oligonucleotide primers.

Each of the PCR primers consists of a gene-specific 3' portion and an upstream universal sequence. The amplification is performed in a multiplex format to increase the assay throughput. The PCR primers are designed in promoter regions that can give optimal PCR amplification, regardless of the number of CpG dinucleotide sites present in that region. At least 3 or more promoter regions can be multiplex amplified in one PCR reaction.

The polymerase is either a native or recombinant thermostable polymerase from *Thermus aquaticus, Thermus thermophilus, Pyrococcus furious*, or *Thermotoga maritime*. The polymerase chain reaction process is fully described in Erlich et al., *Science* 252: 1643-50 (1991); Innis et al., *PCR Protocols: A Guide to Methods and Applications*, Academic Press:

New York (1990); and Saiki et al., *Science* 239: 487-91 (1988), which are hereby incorporated by reference in their entirety.

In carrying out PCR, the target nucleic acid, when present in the form of a double stranded DNA molecule is denatured to separate the strands. This is achieved by heating to a temperature of 80-105° C. Polymerase chain reaction primers are then added and allowed to hybridize to the strands, typically at a temperature of 20-85° C. A thermostable polymerase (e.g., *Thermus aquaticus* polymerase) is also added, and the temperature is then adjusted to 50-85° C. to extend the primer along the length of the nucleic acid to which the primer is hybridized. After the extension phase of the polymerase chain reaction, the resulting double stranded molecule is heated to a temperature of 80-105° C. to denature the molecule and to separate the strands. These hybridization, extension, and denaturation steps may be repeated a number of times to amplify the target nucleic acid to an appropriate level.

In step 4 as shown in FIGS. 2-10, all the desired promoter regions are simultaneously amplified with a universal PCR primer. The universal sequence has been appended to the 5' portion of each gene-specific PCR primer. In this round of PCR amplification, the annealing temperature of PCR reaction is preferably 5° C. lower than the above PCR condition of gene-specific amplification. This lowered annealing temperature ensures all of the first round full length PCR products are amplified at similar efficiencies. Proteinase K (QIAGEN, Valencia, Calif.) is added at the end of the second round multiplex PCR reaction to inactivate the remaining thermostable polymerase. Before pooling the PCR products for further LDR analysis, the presence of the correct PCR fragments are verified by gel or capillary electrophoresis. The universal primer may have a fluorescent reporter to facilitate identification of PCR products on an automated capillary or gel DNA sequencing machine, such as an ABI 3730 or 377.

In a preferred embodiment of the present invention, the same universal primer is used on both the upstream and downstream primers of each PCR primer pair. This design facilitates multiplexed PCR amplification. Regular multiplexed PCR often fails to amplify all desired products. For "n" primer pairs, there are $2n^2+n$ possible classes of PCR amplicons. Thus, as the number of primer pairs increases, the number of potentially false amplicons is squared, including a rapidly increasing probability of forming primer dimers. Once primer dimers form, they will generally amplify faster than the desired amplicon, leading to amplicon dropout and a false negative result.

Bisulfite treated DNA is particularly prone to giving false amplicons. A 16 base region of genomic DNA has a frequency of about 1 in 4 billion bases and is thus unique in the genome. In contrast, when such a 16mer is treated with bisulfite, on average, 4 of the bases will be converted from C to T. Thus, the 16 bases will have about half of the bases as T, in other words, the bisulfite treated sequence will appear once every 16.7 million bases or 179 times in the genome (=3 billion/16.7 million). To attempt to get around this difficulty, primers are made longer and when possible, in regions where the number of changes is optimal for the particular assay. Nevertheless, until this invention, multiplexed PCR amplification of bisulfite treated DNA has been exceedingly difficult if not impossible.

By using the same universal primer on both sides of the amplicon in the second PCR step, spurious amplifications from primer dimers are eliminated. If a primer dimer accidentally forms, it creates a panhandle structure upon denaturation/renaturation, and this inhibits binding of a universal primer, and thus does not amplify. While authentic amplicons also have the same universal sequence on both ends, these are far enough apart such that primer hybridization effectively competes against internal (panhandle) hybridization. In a preferred embodiment, the PCR primers are designed so their 3' ends are between 150 and 500 bp apart. The concentration of the initial PCR primers may be adjusted to assist in obtaining approximately equal amplifications of all the PCR amplicons.

Alternatively, the universal primers may be designed such that they contain some sequence differences, either at the 3' end, the 5' end, internally, or a combination of the above, but still retain greater than 80% identity. By using two universal primers that are slightly different, smaller fragments may be more easily amplified as the two universal primers are less likely to form a panhandle, but primer dimers still do not amplify as the proximity and overall similarity in sequences still favors panhandle formation (and consequently inhibition of amplification).

Multiplexed PCR amplification will occasionally yield additional unanticipated amplicons. However, by using LDR to score methylation status of a particular amplicon, false PCR products are not detected and, consequently, do not interfere with the proper interpretation of the results.

The next step (step 5 as depicted in the process of FIGS. 2-10) is to carry out an LDR procedure to interrogate the methylation status of the cytosines reside in the CpG dinucleotides. Multiple secondary extension products are pooled prior to the ligase detection reaction.

The ligase detection reaction process, in accordance with the present invention, is described generally in U.S. Pat. Nos. 5,494,810, 5,830,711, and 6,054,564 to Barany et al., Barany et al., *Gene* 109:1-11 (1991), and Barany et al., *Proc. Natl. Acad. Sci. USA* 88:189-193 (1991), the disclosures of which are hereby incorporated by reference in their entirety. In accordance with the present invention, the ligase detection reaction can use two sets of complementary oligonucleotides. This is known as the ligase chain reaction which is described in the immediately preceding references, which are hereby incorporated by reference in their entirety. Alternatively, the ligase detection reaction can involve a single cycle which is also known as the oligonucleotide ligation assay. See Landegren et al., *Science* 241:1077-80 (1988); Landegren et al., *Science* 242:229-37 (1988); and U.S. Pat. No. 4,988,617 to Landegren et al., which are hereby incorporated by reference in their entirety.

During the ligase detection reaction phase of the process, the denaturation treatment is carried out at a temperature of 80-105° C., while hybridization takes place at 50-85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase of the process is 1 to 250 minutes.

The ligase used in this invention is a thermostable ligase, such as *Thermus thermophilus, Thermos* species AK16D, *Thermos aquaticus, Pyrococcus furious*, or *Thermotoga maritima*. The thermostable ligase may be derived from *Thermus thermophilus* or it can be prepared recombinantly. Procedures for such isolation as well as the recombinant production of *Thermus thermophilus* ligase as well as *Thermus aquaticus* ligase are disclosed in U.S. Pat. Nos. 5,494,810, 5,830,711, and 6,054,564 to Barany et al., and Barany et al., *Gene* 109: 1-11 (1991); Takahashi et al., *J. Biol. Chem.* 259:10041-47 (1984); Tong et al. *Nucleic Acids Research* 27:788-794 (1999), which are hereby incorporated by reference in their entirety. Some of these references contain complete sequence information for this ligase as well as the encoding DNA.

Other suitable ligases include, without limitation, *E. coli* ligase, T4 ligase, *Thermus* sp. AK16 ligase (U.S. Pat. No. 6,949,370 to Barany et al., which is hereby incorporated by reference), *Aquifex aeolicus* ligase, *Thermotoga maritima* ligase, and *Pyrococcus* ligase. The ligation detection reaction mixture may include a carrier DNA, such as salmon sperm DNA.

The oligonucleotide probe sets can be in the form of ribonucleotides, deoxynucleotides, modified ribonucleotides, modified deoxyribonucleotides, peptide nucleotide analogues, modified peptide nucleic acid analogues, modified phosphate-sugar-backbone oligonucleotides, nucleotide analogs, and mixtures thereof.

In one variation, the oligonucleotides of the oligonucleotide probe sets each have a hybridization or melting temperature (i.e. $T_m$) of 66-70° C. These oligonucleotides are 20-28 nucleotides long.

It may be desirable to destroy chemically or enzymatically unconverted LDR oligonucleotide probes that contain addressable nucleotide array-specific portions after the ligase detection reaction process is completed. Such unconverted probes will otherwise compete with ligation products for hybridization to other nucleic acid molecules during downstream processing. Destruction can be accomplished by utilizing an exonuclease, such as exonuclease III (Guo et al., *Methods in Enzymology* 100:60-96 (1985), which is hereby incorporated by reference in its entirety) in combination with LDR probes that are blocked at the ends and not involved with ligation of probes to one another. The blocking moiety could be a reporter group or a phosphorothioate group (Nikiforow et al., *PCR Methods and Applications* 3:285-291 (1994), which is hereby incorporated by reference in its entirety). After the LDR process, unligated probes are selectively destroyed by incubation of the reaction mixture with the exonuclease. The ligated probes are protected due to the elimination of free 3' ends which are required for initiation of the exonuclease reaction. This approach results in an increase in the signal-to-noise ratio, especially where the LDR reaction forms only a small amount of product. Since unligated oligonucleotides compete for hybridization to other nucleic acid molecules in downstream processing, such competition with the ligated oligonucleotides lowers the signal. An additional advantage of this approach is that unhybridized label-containing sequences are degraded and, therefore, are less able to cause a target-independent background signal, because they can be removed more easily by washing.

One or more gene specific LDR oligonucleotide probes are designed for each of the CpG dinucleotide sites in the LRAT promoter region (See Table 2), or region upstream thereof. A preferred embodiment of this invention includes the design of two discriminating and one common LDR probe for each of the CpG sites. Each of the discriminating probes contains a 5' label (such as a fluorescent label) and the 3' nucleotide discriminates the methylation status of a given cytosine. Preferable labels include chromophores, fluorescent moieties, enzymes, antigens, heavy metals, magnetic probes, infrared dyes, phosphorescent groups, radioactive materials, chemiluminescent moieties and electrochemical detecting moieties. Shown in FIGS. 2-10 of the present invention, Cy5 fluorescent labeled probes are used to detect unmethylated cytosines, while Cy3 fluorescent labeled probes are used to distinguish the methylated cytosines. Each of the common probes is 5' end phosphorylated with a unique zip-code complement sequence attached to its 3' end. The Universal Array comprises a solid support with different capture oligonucleotides immobilized at different particular sites, where the capture oligonucleotides have nucleotide sequences complementary to the addressable array-specific portions. After being subjected to one or more ligase detection reaction cycles, the reaction mixture is contacted with the solid support under conditions effective to hybridize the ligation product sequences to the capture oligonucleotides in a base-specific manner (i.e. at a temperature of 45-90° C. for a period of up to 60 minutes). The LDR products captured on a Universal Array and the fluorescence signals are measured using a microarray scanner. Each address is double spotted to ensure the quality of array fabrication and oligonucleotide hybridization accuracy. The LDR/Universal Array approach has been fully described in Gerry et al., *J. Mol. Biol.* 292: 251-262 (1999); Favis et al., *Natural Biotechnology* 18: 561-564 (2000) which are hereby incorporated by reference in their entirety.

Hybridization may be accelerated by adding volume exclusion or chaotropic agents. When an array consists of dozens to hundreds of addresses, it is important that the correct ligation products have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed sequentially with a low stringency wash buffer and then a high stringency wash buffer.

It is important to select capture oligonucleotide probes and addressable array-specific portions which will hybridize in a stable fashion. This requires that the oligonucleotide probe sets and the capture oligonucleotides be configured so that the oligonucleotide sets hybridize to the target nucleic acid molecules at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The solid support of the array can be made from a wide variety of materials. The substrate may be biological, nonbiological, organic, inorganic, or a combination of any of these, existing as particles, strands, precipitates, gels, sheets, tubing, spheres, containers, capillaries, pads, slices, films, plates, slides, discs, membranes, etc. The substrate may have any convenient shape, such as a disc, square, circle, etc. The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface is also chosen to provide appropriate light-absorbing characteristics. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polyethylene, polypropylene, polyvinyl chloride, poly(methyl acrylate), poly(methyl methacrylate), or combinations thereof. Other substrate materials will be readily apparent to those of ordinary skill in the art upon review of this disclosure. In a preferred embodiment, the substrate is flat glass or single-crystal silicon.

A variety of commercially-available materials, which include suitably modified glass, plastic, or carbohydrate surfaces or a variety of membranes, can be used. Depending on the material, surface functional groups (e.g., silanol, hydroxyl, carboxyl, amino) may be present from the outset (perhaps as part of the coating polymer), or will require a separate procedure (e.g., plasma amination, chromic acid oxidation, treatment with a functionalized side chain alkyltrichlorosilane) for introduction of the functional group.

The surface of the functionalized substrate is preferably provided with a layer of linker molecules, although it will be understood that the linker molecules are not required elements of the invention. The linker molecules are preferably of sufficient length to permit polymers in a completed substrate to interact freely with molecules exposed to the substrate. The linker molecules should be 6-50 atoms long to provide sufficient exposure. The linker molecules may be, for example, aryl acetylene, ethylene glycol oligomers containing 2-10 monomer units, diamines, diacids, amino acids, or combinations thereof.

Further details regarding solid supports, functional groups, and linkers are set forth in U.S. Pat. Nos. 6,852,487 and 7,083,917 to Barany et al., which are hereby incorporated by reference in their entirety. Techniques for improving the performance of addressable arrays is set forth in U.S. Pat. No. 6,506,594 to Barany et al., which is hereby incorporated by reference in its entirety.

As a result, the addressable array-specific portions are captured on the solid support at the site with the complementary capture oligonucleotide. The presence of ligation product sequences captured using the addressable array-specific portions and immobilized to the solid support at particular sites indicates the methylation status of the target nucleotide sequences in the sample.

Alternatively, the LDR probes may be designed such that the products have different mobility when separated by gel or capillary electrophoresis, and products are separated and distinguished by their unique fluorescent label and their size or electrophoretic mobility (Day et al., *Genomics* 29:152-162 (1995); Belgrader et al., *Genome Science and Technology* 1:77-87 (1996); and Day et al., *Human Molecular Genetics* 5:2039-2048 (1996), which are hereby incorporated by reference in their entirety).

The methylation analysis process described herein is used to distinguish a presence of low abundance methylated target nucleic acid molecule in the sample from a presence of a majority of unmethylated target nucleic acid molecule in the sample. This may involve situations where the presence of low abundance methylated target nucleic acid molecule in the sample may be distinguished in the presence of a 10 to 100-fold excess, preferably 10 to 1,000-fold excess, more preferably 100 to 10,000-fold excess, and most preferably 10,000 to 100,000-excess of unmethylated target nucleic acid molecules, in the sample.

Another aspect of the methylation analysis is the ability to quantify the degree of methylation at a given genomic region, such as the LRAT promoter region, within a biological sample. This is an important feature of a robust DNA methylation assay, particularly when applying it to mostly heterogeneous clinical samples. For example, a solid tumor sample is often composed of both tumor cells and normal infiltrating cells. Further, different genes may have undergone methylation silencing during progression of the tumor, and the degree or progression of that silencing may be clinically relevant (Cui et al., *Science* 299:1753-1755 (2003); Cui et al., *Cancer Research* 62: 6442-6446 (2002), which have been incorporated by reference in their entirety).

Since the present invention teaches both PCR primer and LDR probe design which do not bias amplification or detection of methylation status, independent of methylation status of neighboring CpG dinucleotides (i.e. by using nucleotide analogues or degenerate bases within the primer designs), it is possible to quantify methylation level at a given site. As described above, methylation level may be assayed by two related approaches. In the first, the methylation level (percentage of methylation) of each interrogated cytosine can also be calculated by dividing the total number of methylated signals at a specific CpG site by the sum of methylated and unmethylated signals at the same CpG site. This is calibrated against known mixtures of methylated and unmethylated. DNA, or synthetic substrates corresponding to the sequence resulting from PCR amplification of methylated and unmethylated DNA, respectively. In a second approach, the overall methylation level of each LRAT promoter nucleotide sequence, or regions upstream thereof, can be obtained by calculating the average level of methylation across some or all of the interrogated cytosines within the promoter nucleotide sequence, or region upstream thereof.

A second aspect of the present invention relates to a method of determining a prognosis for a subject having cancer This method includes assessing the level of LRAT mRNA expression in a sample obtained from the subject and comparing the level of LRAT mRNA expression in the sample to the level of LRAT mRNA expression in a reference RNA standard. A decrease in LRAT mRNA expression in the sample compared to the reference standard indicates a favorable prognosis for the subject.

In a preferred embodiment of the method of the present invention, the reference RNA standard comprises a matched normal tissue sample obtained from the same subject that the test sample is obtained from. For example, LRAT mRNA expression is assessed in a tumor tissue, such as colon cancer tissue, obtained from the subject. The level of LRAT mRNA expression in this sample is compared to the level of LRAT mRNA expression in a matched normal tissue, such as normal colon tissue, also obtained from said subject. A decrease in the level of LRAT mRNA expression in the tumor tissue sample compared to the matched normal tissue indicates a favorable prognosis of the subject having cancer. In another example, the level of LRAT mRNA expression is assessed in disease sample, such as RNA isolated from stool of subject with colon cancer. The level of LRAT mRNA expression in this sample is compared to the level of LRAT mRNA expression in a pre-disease sample, such as RNA isolated from stool of said subject prior to having cancer. A decrease in LRAT mRNA expression in the disease sample compared to the pre-disease sample indicates a favorable prognosis for the subject having cancer.

The cancer types and states to be evaluated in accordance with this aspect of the present invention are substantially the same as described above.

Sample RNA from the subject can be isolated and prepared from tissue or cells using methods known in the art. The RNA preparation must produce enzymatically manipulatable mRNA or analyzable RNA. The RNA may be isolated using the guanidinium isothiocyanate-ultracentrifugation method, the guanidinium and phenol-chloroform method, the lithium chloride-SDS urea method or the poly A+/mRNA from tissue lysates using oligo (dT) cellulose method. It is important that the quality and quantity of the RNA yield is accessed prior to quantitative gene expression analysis. Total isolated RNA can be used to generate first strand copy DNA (cDNA) using any known procedure in the art, for example, using random primers, oligo-dT primers, or random-oligo-dT primers. The cDNA can then be used as a template for a first round amplification reaction or for the quantitative PCR reaction depending on target or sample abundance. The first round PCR amplification is performed with a primer set, including forward and reverse primers, that are specific for the target gene of interest. Following the first round of amplification, a cleaned portion of the reaction product is used for quantitative analysis. Quantitative real-time PCR protocols typically rely on fluorescent detection of product formation following the extension phase of the reaction cycle. Typical fluorescent approaches for quantitative PCR are based on a fluorescent reporter dyes such as SYBR green, FAM, fluorescein, HEX, TET, TAMRA, etc. and quencher dyes such as DABSYL, Black Hole, etc. Systems, such as Molecular Beacons (Integrated DNA Technologies, Coralville, Iowa), Taqman Probes® (Applied Biosystems, Foster City, Calif.), or Scorpion® Primers (DxS Ltd., Manchester, UK) are also well known in the art of quantitative gene analysis. Examples of methods and reagents related to real time probes can be found in U.S. Pat. Nos. 5,925,517, 6,103,476, 6,150,097, and 6,037,130 all to Tyagi et al., which are hereby incorporated by reference in their entirety.

Quantitative gene expression can be expressed as absolute copy number or as relative gene expression. Both methods utilize a standard curve from which to accurately obtain quantitative data from. Alternatively, relative gene expression can also be calculated using the Comparative $C_T$ Method as described in the ABI Prism 7700 Sequence Detection System User Bulletin #2 which is hereby incorporated by reference in its entirety. The Comparative $C_T$ method is similar to the standard curve method, except it uses an arithmetic formula to calculate the relative gene expression data. A detailed description of absolute and relative gene expression quantitation is provided in the ABI Prism 7700 Sequence Detection System User Bulletin #2, which is hereby incorporated by reference in its entirety. A preferable embodiment of this aspect of the invention, is the analysis of LRAT gene expression in cancerous and non-cancerous tissues which is described herein (Examples 8-9).

A third aspect of the present invention relates to a method of determining the prognosis of a subject having cancer. This method includes assessing the level of LRAT protein expression in a sample obtained from the subject and comparing the level of LRAT protein expression in the sample to the level of LRAT protein expression in a reference protein standard. A decrease in LRAT protein expression in the sample compared to the reference standard indicates a favorable prognosis for the subject.

In a preferred embodiment of the method of the present invention, the reference protein standard comprises a matched normal tissue sample obtained from the same subject that the test sample is obtained from. For example, LRAT protein expression is assessed in a tumor tissue, such as colon cancer tissue, obtained from the subject. The level of LRAT protein expression in this sample is compared to the level of LRAT protein expression in a matched normal tissue, such as normal colon tissue, also obtained from said subject. A decrease in the level of LRAT protein expression in the tumor tissue sample compared to the matched normal tissue indicates a favorable prognosis for the subject having cancer. In another example, the level of LRAT protein expression is assessed in disease sample, such as protein isolated from stool of subject with colon cancer. The level of LRAT protein expression in this sample is compared to the level of LRAT protein expression in a pre-disease sample, such as protein isolated from stool of said subject prior to having cancer. A decrease in LRAT protein expression in the disease sample compared to the pre-disease sample indicates a favorable prognosis for the subject having cancer.

The cancer types and states to be evaluated in accordance with this aspect of the present invention are substantially the same as described above.

Sample protein from the subject can be isolated and prepared from tissue or cells using standard preparation methods known in the art. For example, tissue and cells can be lysed in buffer containing a detergent, such as sodium dodecyl sulfate (SDS), and a cocktail of protease inhibitors. Protein yield can be determined using the Bradford Assay or any variation of the method known in the art. Assessing the level of expression of a target protein within a sample can be performed by various techniques known in the art, For example, assessing the level of expression can involve analyzing one or more proteins by two-dimensional gel electrophoresis, mass spectroscopy, high performance liquid chromatography (HPLC), fast protein liquid chromatography, multi-dimensional liquid chromatography followed by tandem mass spectrometry, or protein chip expression analysis. Other techniques, using antibodies or other agents which selectively bind to the protein of interest, commonly used for assessing protein expression include Western Blot, immunoprecipitation, enzyme-linked immunosorbent assay (ELISA), radioimmunoassay (RIA), or fluorescent activated cell sorting (FACS). Immunohistochemical and immunofluorescent techniques in which antibody binding to specific protein target is visualized within a whole cell or whole tissue sample is also contemplated.

A fourth aspect of the present invention relates to a method of treating a subject for cancer. The method includes treating a subject with a pharmaceutical composition which inhibits LRAT expression and activity under conditions effective to treat said cancer. A pharmaceutical composition refers to one that is physiologically tolerable with low to no toxic side effects when administered to a human.

In a preferred embodiment of the present invention, a treatment regimen is specifically tailored for the subject having cancer. Such treatment regimen is determined by collecting genomic DNA samples from the subject and determining the level of LRAT methylation in the samples. Alternatively, such treatment regimen is determined by collecting samples from the subject and determining the level of LRAT mRNA or protein expression. Based on the level of LRAT methylation or LRAT mRNA or protein expression, a therapeutic treatment regimen can be determined and the subject can be administered an optimal dose of a pharmaceutical composition which inhibits LRAT expression and activity. Further, samples from the subject can be collected at various time points during the course or progression of the disease and the level of LRAT methylation or LRAT mRNA and protein expression can be monitored. Depending on changes in the level of LRAT methylation or LRAT expression, the dosage of the pharmaceutical composition which inhibits LRAT activity can be adjusted accordingly.

Chemical compositions which inhibit the activity of LRAT are known in the art. The active site of LRAT contains a cysteine residue which directs the cleavage of fatty acid from phospholipid and its subsequent transfer to retinol. Chemical composition which target this cysteine residue, including sulfhydryl-directed reagents such as iodoacetamide and p-chloromercuriphenylsulfonic acid (PCMS) are potent LRAT inhibitors. (Schmitt and Ong, "Expression of Cellular Retinol-Binding Protein and Lecithin-Retinol Acyltransferase in Developing Rat Testis," *Biology of Reproduction* 49:972-979 (1993), which is hereby incorporated by reference in its entirety). Likewise, additional potent inhibitors of LRAT include N-ethylmaleimide, p-aminophenylarsineoxide, and phenylmethylsulfonyl fluoride which also react with the cysteine moiety. (Herr et al., "Solubilization and Partial Characterization of Lecithin-Retinol Acyltransferase from Rat Liver," *J. Nutr. Biochem.* 2(9):503-511 (1991), which is hereby incorporated by reference in its entirety). Other LRAT inhibitors suitable for the present invention include, but are not limited to, retinyl bromoacetates as described by Trevinoa et al., "Lecithin:Retinol Acyltransferase in ARPE-19," *Experimental Eye Research* 80(6):897-900 (2005) which is hereby incorporated by reference in its entirety, and N-boc-L-biocytinyl-11-aminoundecane chloromethyl ketone as described by Ruiz et al., "Genomic Organization and Mutation Analysis of the Gene Encoding Lecithin Retinol Acyltransferase in Human Retinal Pigment Epithelium," *Inv. Opthalmology & Visual Sci.* 42(1):31-37 (2001) which is hereby incorporated by reference in its entirety.

In another embodiment, the pharmaceutical composition which inhibits LRAT is in the form of a biological composition. Such biological inhibitors include functional nucleic acids, that bind to and inhibit LRAT (DNA, RNA polypeptide, or carbohydrate chain) thereby preventing its expression and subsequent activity. Functional nucleic acids include antisense molecules, aptamers, ribozymes, triplex forming molecules, and external guide sequences.

The use of antisense methods to inhibit the in vitro translation of genes is well known in the art (see, e.g., Marcus-Sakura, *Anal. Biochem.* 172:289 (1988) which is hereby incorporated by reference in its entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an RNA molecule (e.g., an mRNA molecule) (see, e.g., Weintraub, *Scientific American* 262:40 (1990) which is hereby incorporated by reference in its entirety). The antisense nucleic acids hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced by, for example, using gene therapy methods.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules as well as large molecules as described in (U.S. Pat. Nos. 5,631,146; 5,786,462; 5,543,293; and 5,580,737 which are all hereby incorporated by reference in their entirety.) Aptamers can bind very tightly with $k_d$s from the target molecule of less than $10^{-12}$ M. It is preferred that the aptamers bind the target molecule with a $k_d$ less than $10^{-6}$. It is more preferred that the aptamers bind the target molecule with a $k_d$ less than $10^{-8}$. Aptamers can bind the target molecule with a very high degree of specificity Also suitable for the inhibition of LRAT are ribozymes, (for example, U.S. Pat. No. 5,334,711 to Sproat et al, U.S. Pat. No. 5,646,031 to DeYoung et al, U.S. Pat. No. 5,595,873 to Joyce et al., and U.S. Pat. No. 5,580,967 to Joyce et al., all of which are hereby incorporated by reference in their entirety) triplex forming functional nucleic acid molecules (U.S. Pat. No. 5,176,996 to Hogan et al., which is hereby incorporated by reference in its entirety) or external guide sequences (EGSs) (WO 92/03566 by Yale, and Forster and Altman, Science 238:407-409 (1990) which are hereby incorporated by reference).

In another embodiment, the inhibitor of LRAT can be a protein, polypeptide or antibody that can bind to and inhibit LRAT expression and activity. Antibodies that specifically recognize LRAT, can be for example, monoclonal polyclonal, or single-chain antibodies. Additionally, antibodies can be chimeric or hybrid antibodies, with dual or multiple antigen or epitope specificities. Such antibodies and fragments can be made by techniques known in the art and can be screened for specificity and activity according to the methods also know in the art (See Harlow and Lane. Antibodies, A Laboratory Manual. Cold Spring Harbor Publications, New York, (1988)). Preferably, antibodies of the present invention are humanized for administration in human subjects.

A preferred embodiment of the present invention further includes treating a subject with a pharmaceutical composition which inhibits LRAT activity as described above in combination with one or more other standard cancer therapeutic treatments.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

EXAMPLES

Example 1

Reagents and Media

All routine chemical reagents were purchased from Sigma Chemicals (St. Louis, Mo.) or Fisher Scientific (Fair Lawn, N.J.). Deoxyoligonucleotides were ordered from Integrated DNA Technologies Inc. (Coralville, Iowa). PCR buffer and AmpliTaq Gold were purchased from Applied Biosystems (Foster City, Calif.). Human genomic DNA was purchased from Roche (Indianapolis, Ind.). Colorectal, breast, and prostate cancer cell lines were obtained from American Type Culture Collection (ATCC) (Manassas, Va.) and cultured under the ATCC recommended media conditions. Fresh frozen primary colorectal adenocarcinomas were obtained from Memorial Sloan Kettering Cancer Center (New York, N.Y.) under IRB approved protocols. SssI methylase was purchased from New England BioLabs (Beverly, Mass.). Proteinase K was purchased from QIAGEN (Valencia, Calif.).

A 20 µl ligase detection reaction (LDR) contains 20 mM Tris pH 7.6, 10 mM $MgCl_2$, 100 mM KCl, 10 mM DTT, 0.5 mM NAD, 25 mM Tth ligase, 250 fmol LDR primers and pooled multiplex PCR products. Tth ligase storage buffer contains 10 mM Tris pH 8.5, 1 mM EDTA, 1 mM DTT, 200 mg/ml BSA, 50% glycerol. Tth ligase dilution buffer contains 15 mM Tris pH 7.6, 7.5 mM $MgCl_2$, 0.15 mg/ml BSA.

Example 2

Sodium Bisulfite Treatment of Genomic DNAs

Sodium bisulfite has been widely used to distinguish 5-methylcytosine from cytosine. Bisulfite converts cytosine into uracil via a deamination reaction while leaving 5-methylcytosine unchanged. Genomic DNAs extracted from tumor cell lines and colon tumor samples were used in this study. Typically, 1~0.5 µg genomic DNA in a volume of 40 µl was incubated with 0.2N NaOH at 37° C. for 10 minutes. Next, 30 µl of freshly made 10 mM hydroquinone and 520 5,580,9671 of freshly made 3M sodium bisulfite were added to the reaction. Sodium bisulfite (3M) was made with 1.88 g sodium bisulfite (Sigma Chemicals, ACS grade) dissolved in a final total of 5 ml deionized $H_2O$ at pH 5.0. The bisulfite/DNA mixture was incubated for 16 hours in a DNA thermal cycler (Perkin Elmer Cetus) with the cycles of 50° C. for 20 minutes followed by a denaturation step at 85° C. for 15 seconds. The bisulfite treated DNAs were desalted using MICROCON centrifugal filter devices (Millipore, Bedford, Mass.) or, alternatively, were cleaned with Wizard DNA clean-up kit (Promega, Madison, Wis.). The eluted DNAs were incubated with one-tenth volume of 3N NaOH at room temperature for 5 minutes before ethanol precipitation. The DNA pellet was then resuspended in 20 µl deionized $H_2O$ and stored at 4° C. until PCR amplification.

Example 3

Multiplex PCR Amplification

Two promoter regions of the LRAT gene were simultaneously amplified in a multiplex fashion. The multiplex PCR has two stages, namely a gene-specific amplification (stage one) and a universal amplification (stage two). The PCR primers are shown in Table 1.

The gene-specific PCR primers were designed such that the 3' sequence contains a gene-specific region and the 5' region contains an universal sequence. The gene specific primers were designed to hybridize to promoter regions containing as few CpG sites as possible. For primers that inevitably include one or more CpG dinucleotides, the nucleotide analogs, K and P, which can hybridize to either C or T nucleotides or G or A nucleotides, respectively, can be included in the primer design. To reduce the cost of primer synthesis, PCR primers were designed without nucleotide analogs and using nucleotides G to replace K (purine derivative) and T to replace P (pyrimidine derivative), respectively (Table 1). This type of primer design favors pairing to DNA that was initially methylated, although it also allows the mismatch pairing of G/T when the original DNA was unmethylated at that site. The ethidium bromide staining intensity of PCR amplicons separated by the agarose gel electrophoresis, demonstrated that this primer design was as robust as using analogs-containing primers.

TABLE 1

| PRIMERS | SEQUENCE (5' to 3') | CONC. in PCR |
|---|---|---|
| LRAT RP1 SEQ ID NO: 3 | CGCTGCCAACTACCGCACATCTTATTTTTTATTGTGGTTTGGTTGAGTC | 1.25 pmol |
| LRAT FP1 SEQ ID NO: 4 | CGCTGCCAACTACCGCACATCACCTCCAACATAAAATTCTTCATCCTAC | 1.25 pmol |
| LRAT RP3 SEQ ID NO: 5 | CGCTGCCAACTACCGCACATCATAATCGTGTTGTTTATATGATGTTCGATA | 2.5 pmol |

TABLE 1-continued

| PRIMERS | | SEQUENCE (5' to 3') | CONC. in PCR |
|---|---|---|---|
| LRAT FP3 | SEQ ID NO: 6 | CGCTGCCAACTACCGCACATCCACAACAAACTATAAAAAATAAAACCCAAC | 2.5 pmol |
| UniB2 | SEQ ID NO: 7 | CGCTGCCAACTACCGCACATC | 12.5 pmol |

In the first stage, the multiplex PCR reaction mixture (12.5 μl) consisted of 0.5 μl bisulfite modified DNA, 400 μM of each dNTP, 1× AmpliTaq Gold PCR buffer, 4 mM $MgCl_2$, and 1.25 U AmpliTaq Gold polymerase. The gene-specific PCR primer concentrations are listed in the Table 1. Mineral oil was added to each reaction before thermal cycling. The PCR procedure included a pre-denaturation step at 95° C. for 10 minutes, 15 cycles of three-step amplification with each cycle consisting of denaturation at 94° C. for 30 second, annealing at 60° C. for 1 minute, and extension at 72° C. for 1 minute. A final extension step was at 72° C. for 5 minutes.

The second stage of multiplex PCR amplification was primed from the universal sequences (UniB) located at the extreme 5' end of the gene-specific primers. The second stage PCR reaction mixture (12.5 μl) consisted of 400 μM of each dNTP, 1× AmpliTaq Gold PCR buffer, 4 mM $MgCl_2$, 12.5 pmol universal primer B (UniB) and 1.25 U AmpliTaq Gold polymerase. The UniB PCR primer sequence is listed in the Table 1. The 12.5 μl reaction mixtures were added through the mineral oil to the finished first stage PCR reactions. The PCR procedure included a pre-denaturation step at 95° C. for 10 minutes, 30 cycles of three-step amplification with each cycle consisting of denaturation at 94° C. for 30 second, annealing at 55° C. for 1 minute, and extension at 72° C. for 1 minute. A final extension step was at 72° C. for 5 minutes.

After the two-stage PCR reaction, 1.25 μl Qiagen Proteinase K (approximately 20 mg/ml) was added to the total 25 μl reaction. The Proteinase K digestion condition consisted of 70° C. for 10 minutes and 90° C. for 15 minutes.

Example 4

Ligase Detection Reaction and Hybridization to Universal Array

Ligation detection reaction was carried out in a 20 μl volume containing 20 mM Tris-HCl pH 7.6, 10 mM $MgCl_2$, 100 mM KCl, 20 mM DTT, 1 mM NAD, 50 fmol wild type Tth ligase, 500 fmol each of LDR probes, 5-10 ng each of the PCR amplicons. The Tth ligase may be diluted in a buffer containing 15 mM Tris-HCl pH 7.6, 7.5 mM $MgCl_2$, 0.15 mg/ml BSA. To ensure the scoring accuracy of a promoter methylation status, 30 LDR probes were designed to interrogate the methylation levels of ten CpG dinucleotide sites within the PCR amplified regions. Two discriminating LDR probes and one common LDR probe were designed for each of the CpG sites. The LDR probe mix contains 60 discriminating probes (30 probes for each channel) and 10 common probes (Table 2). The reaction mixtures were preheated for 3 minutes at 95° C., and then cycled for 20 rounds of 95° C. for 30 seconds and 60° C. for four minutes.

The LDR reaction (20 μl) was diluted with equal volume of 2× hybridization buffer (8×SSC and 0.2% SDS), and denatured at 95° C. for 3 minutes then plunged on ice. The Universal Arrays (Amersham Biosciences, Piscataway, N.J.) were assembled with ProPlate slide moduals (Grace Bio-Labs, Bend, Oreg.) and filled with the 40 μl denatured LDR mixes. The assembled arrays were incubated in a rotating hybridization oven for 60 minutes at 65° C. After hybridization, the arrays were rinsed briefly in 4×SSC and washed in 2×SSC, 0.1% SDS for 5-10 minutes at 63.5° C. The fluorescent signals were measured using a ProScanArray scanner (Perkin Elmer, Boston, Mass.).

TABLE 2

Probe Sequences for Ligase Detection Reaction

| PRIMERS | SEQUENCE (5' to 3') |
|---|---|
| LRAT 53T | (Cy5) TGTTATTT TT TAT TGT GGT TTG GTT GAG TTG GTT (SEQ ID NO: 8) |
| LRAT 172Tb | (Cy5) TTGTTTTTTTTTTTT TTT AGT GGT TGT ATT TTG TGT T (SEQ ID NO: 9) |
| LRAT 218T | (Cy5) TTTTGTC GGA GTG GTA TTG GTA TTT TTT TAA GAT (SEQ ID NO: 10) |
| LRAT 222T | (Cy5) GGTTTGTAGG TGA GTA GTA GTG TAG TAT TTT TGT TTG GT (SEQ ID NO: 11) |
| LRAT 242Tb | (Cy5) GTGTAGTATTTTTGT TTG GTG AGT TTA ATT TGT TTA GTT T (SEQ ID NO: 12) |
| LRAT 263T | (Cy5) TTAATTTGTT TAG TTT GGT TTT TGT TGG AGT GGT ATT (SEQ ID NO: 13) |
| LRAT2nd 40T | (Cy5) TTTATATGA TGT TTG ATA TTT TGT TGG TTT TGA TAG AT (SEQ ID NO: 14) |
| LRAT2nd 91T | (Cy5) GTAGAAGGTGG TTT TTA ATA AGT GTT TTA TTT TGG GT (SEQ ID NO: 15) |
| LRAT2nd 145T | (Cy5) GTATTCGCG TGG ATA TAG TGG AGG ATT TTG TTT AT (SEQ ID NO: 16) |
| LRAT2nd 218T | (Cy5) TAGAAAAAGGTATTG TTT AAT GAG GAG GTG GTG T (SEQ ID NO: 17) |
| LRAT 53C | (Cy3) ATTTTTTATTGTGGTTTGGTTGAGTC GGTC (SEQ ID NO: 18) |
| LRAT 172C | (Cy3) TTTTTTTTTAGCGGTCGTATTTTGCG TC (SEQ ID NO: 19) |
| LRAT 218C | (Cy3) TGTCGGAGTGGTATCGGTATTTTTTT AAGAC (SEQ ID NO: 20) |
| LRAT 222C | (Cy3) GTAGGTGAGTAGTAGCGTAGTATTTT TGTTCGGC (SEQ ID NO: 21) |

TABLE 2-continued

| Probe Sequences for Ligase Detection Reaction | |
|---|---|
| PRIMERS | SEQUENCE (5' to 3') |
| LRAT 242C | (Cy3) TTTTGTTCGGCGAGTTTAATTTGTTT AGTTC (SEQ ID NO: 22) |
| LRAT 263C | (Cy3) TGTTTAGTTCGGTTTTTGTCGGAGTG GTATC (SEQ ID NO: 23) |
| LRAT2nd 40C | (Cy3) ATATGATGTTCGATATTTTGTTGGTT TTGATAGAC (SEQ ID NO: 24) |
| LRAT2nd 91C | (Cy3) GGTGGTTTTTAATAAGCGTTTTATTT TGGGC (SEQ ID NO: 25) |
| LRAT2nd 145C | (Cy3) TCGCGTGGATATAGTGGAGGATTTCG TTTAC (SEQ ID NO: 26) |
| LRAT2nd 218C | (Cy3) GGTATTGTTTAACGAGGAGGTGGCGC (SEQ ID NO: 27) |
| 1LRAT 53C (Z18) | pGTTAGGTTTCGTTGTTTTTTTTTGTTTTTTT TTTTTTTTAGGGAGGCTGCTGTCCTTTCGAT CA (SEQ ID NO: 28) |
| 2LRAT 172C (Z19) | pGTATTTTATTTGGTTTGTAGGTGAGTAGTAG CGTAGTATTTTTGACAGCGTGTTCGTTGCTTG CATCA (SEQ ID NO: 29) |
| 3LRAT 222Cc (Z31) | pGAG TTT AAT TTG TTT AGT TCG GTT TTT GTT GGATTGCGGGAACTCACGAGGTCG TAT (SEQ ID NO: 30) |
| 4LRAT 242Cb (Z20) | pGGTTTTTGTCGGATGGTATTGGTATTTTTTT AATGGCGATGGTCCACTCGCAATCA (SEQ ID NO: 31) |
| 5LRAT 263Cb (Z32) | pGGT ATT TTT TTA AGA CGT TTT TTT TTT TGT AGG ATGGCACGGCTCGATAGGTC AAGCTTT (SEQ ID NO: 32) |
| 6LRAT 218C (Z30) | pGTTTTTTTTTTTGTAGGATGAAGAATTTTAT GTTGGAGGCATCGCACTTCGCTTTGCTGATT (SEQ ID NO: 33) |
| 7LRAT2nd 40C (Z10) | pGAT ATG GGG TGT ACG TAG AAG GTG GTT TTTACAAGGCACGTCCCAGACGCATCAA (SEQ ID NO: 34) |
| 8LRAT2nd 91C (Z11) | pGTT ATT GTT AAA GTG GTT AGT ATT TGC GTG GAT ATATGGCACGGGAGCTGACG ACGTGTCAA (SEQ ID NO: 35) |
| 9LRAT2nd 145C (Z12) | pGGAGTTAATATTTTGGTTAATTATTTGGACG AGTTTTTTTAGACGCACCGCAACAGGCTGTC AA (SEQ ID NO: 36) |
| 10LRAT2nd 218C (Z13) | pGGAGGGTTGAAAAGTTGTTGGGTTTTATTTT TCATCGCTGCAAGTACCGCACTCAA (SEQ ID NO: 37) |

Example 5

Determination of Cytosine Methylation Levels at CpG Dinucleotide Sites

LDR is a single tube multiplex reaction with three probes interrogating each of the selected CpG sites. LDR products are captured on a Universal microarray using the ProPlate system (Grace BioLabs) where 64 hybridizations (four slides with 16 sub-arrays each) are carried out simultaneously. Each slide is scanned using a Perkin Elmer ProScanArray (Perkin Elmer, Boston, Mass.) under the same laser power and PMT within the linear dynamic range. The Cy3 and Cy5 dye bias were determined by measuring the fluorescence intensity of an equal quantity of Cy3 and Cy5 labeled LDR probes manually deposited on a slide surface. This fluorescence intensity ratio ($W=I_{Cy3}/I_{Cy5}$) was used to normalize the label bias when calculating the methylation ratio Cy3/(Cy3+Cy5). The methylation standard curves for each interrogate CpG dinucleotide using various combinations of in vitro methylated and unmethylated normal human lymphocyte genomic DNAs were established. The methylation levels of six CpG dinucleotides in the 5'-UTR regions were averaged and used to determine the overall promoter methylation status of LRAT gene.

Example 6

Quantitative Aspect of Bisulfite/PCR-PCR/LDR/Universal Array

Since the present invention teaches both PCR primer and LDR probe design which does not bias amplification or detection of methylation status, independent of methylation status of neighboring CpG dinucleotides (i.e. by using nucleotide analogues or degenerate bases within the primer designs), it is possible to quantify methylation status of given CpG sites in the genome.

Figure 13:
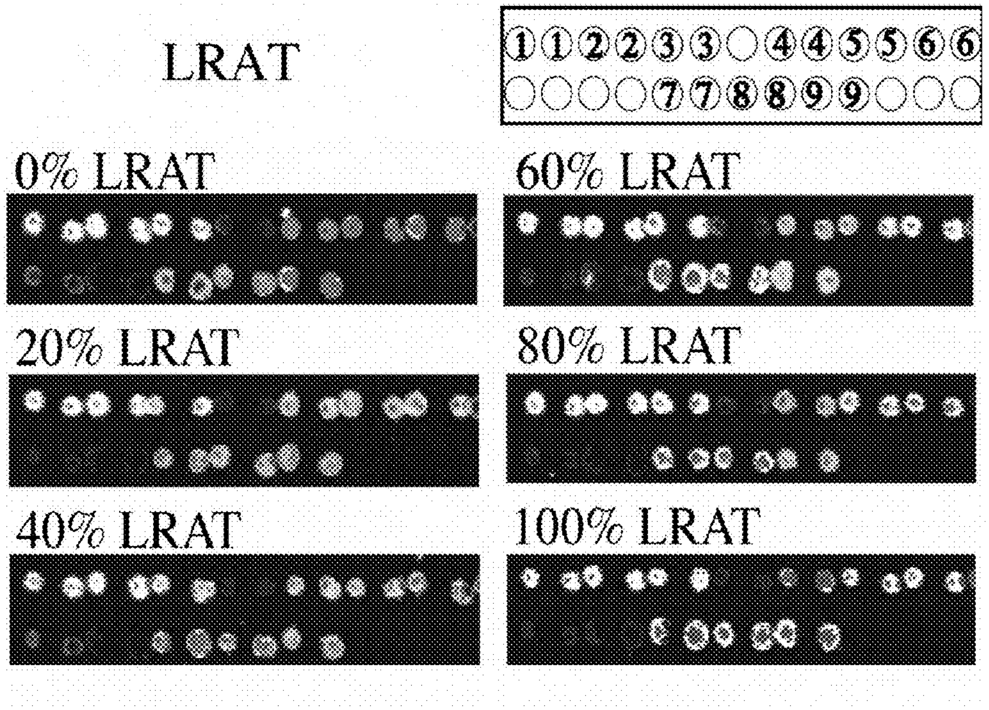
FIG. 13 shows the universal array images for a quantitative analysis of cytosine methylation status at nine selected CpG dinucleotide sites. In vitro methylated and normal human lymphocyte genomic DNAs were mixed in 0%, 20%, 40%, 60%, 80%, and 100% ratios and subjected to Bisulfite-PCR/LDR/Universal Array analysis. Representative array images are shown scanned in both Cy3 and Cy5 channels. Cy3 and Cy5 represent the methylated and unmethylated alleles of CpG dinucleotides, respectively. Color composites of the two channels reflect the methylation levels. Each zip-code was double spotted on the array to ensure array fabrication quality.

To demonstrate that the assay is quantitative, genomic DNA in vitro methylated with SssI methylase was mixed with normal human lymphocytes DNA (carrying unmethylated alleles), such that the test samples contained 0%, 20%, 40%, 60%, 80%, and 100% of methylated alleles and these mixtures were subjected to Bisulfite-PCR/LDR/Universal Array analysis. As shown in FIG. 13, nine CpG dinucleotides located at the 5' regulatory region of LRAT promoter were interrogated. The fluorescence intensity is presented by Cy3 (methylated alleles) or Cy5, (unmethylated alleles) on each double spotted zipcode addresses. The average fluorescence intensity of two duplicated spots was used to calculate the methylation ratio of each analyzed cytosine using the formula $Cy3_{average}/(Cy3_{average}+Cy5_{average})$.

Figure 14:
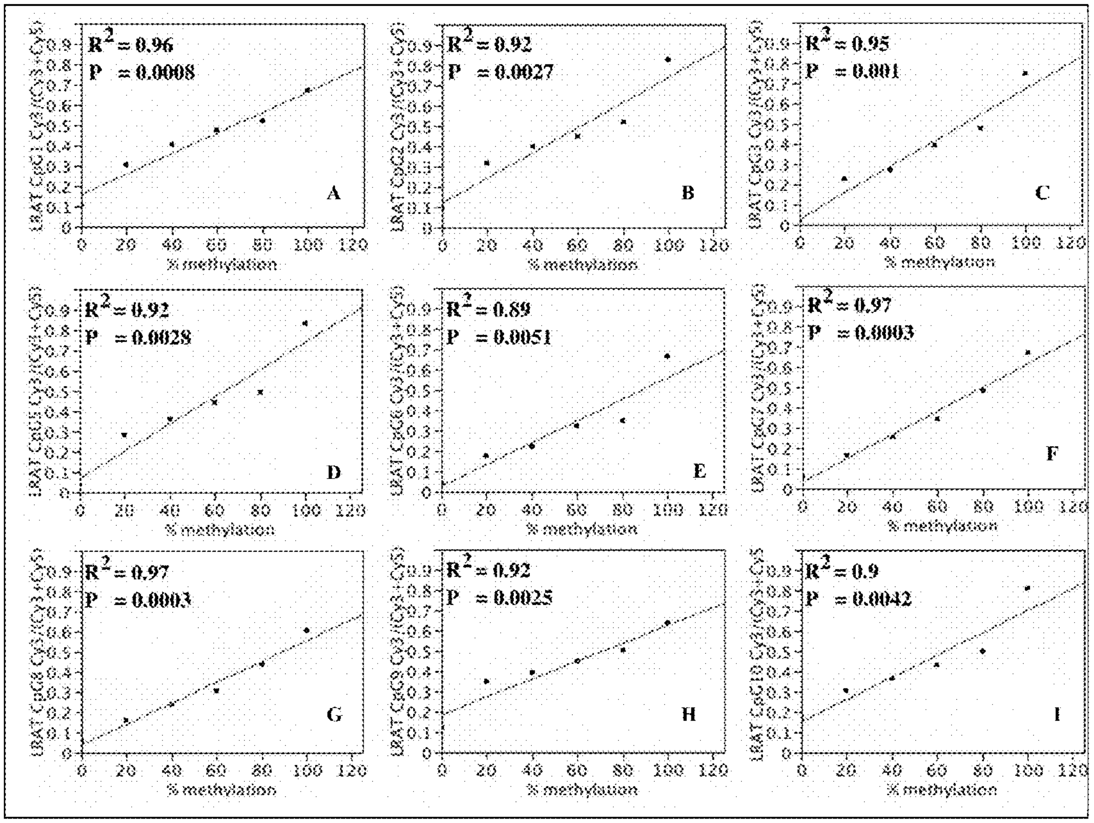
FIGS. 14A-I show quantitative standard curves of methylation at nine CpG dinucleotides in the LRAT promoter. The quantitative methylation levels were determined and extracted from data shown in FIG. 13. In vitro methylated and normal human lymphocyte genomic DNAs were mixed in 0%, 20%, 40%, 60%, 80%, and 100% ratios and subjected to Bisulfite-PCR/LDR/Universal Array analysis. The Y-axis represents the fluorescence intensity Cy3/(Cy3+Cy5) ratio. The X-axis represents the percentage of theoretically methylated genomic DNAs. The $R^2$ and P values of each linear regression line are indicated.

As shown in FIG. 14, the measured methylation ratios of each interrogate cytosine was plotted against the methylation levels of mixed genomic DNAs. The $R^2$ values (correlation coefficient) of these experiments are between 0.97 and 0.89, which demonstrates the linearity of the described assay. Such standard curves can be used as reference points for further measurements clone in clinical samples. Similar standard curves were also established previously for genes such as $p16^{INK4a}$, $p14^{ARF}$, TIMP3, APC, RASSF1, ECAD, MGMT, DAPK, GSTP1 and RARβ (Cheng et al., *Genome Res.* 16(2): 282-289 (2006), which is hereby incorporated by reference in its entirety). In "100%" in vitro methylated DNA sample, the $Cy3_{average}/(Cy3_{average}+Cy5_{average})$ ratios of the investigated CpG sites were between 0.6 and 0.9. This observation suggested that in vitro methylation is not fully efficient due to sequence context variation of each CpG site. This analysis also confirmed the different percentage of methylation at each CpG dinucleotide and suggested that methylation level is not 100% at each CpG site in cell line DNA (Cheng et al., *Genome Res.* 16(2):282-289 (2006), which is hereby incorporated by reference in its entirety). By comparing the ratio of (methylated):(methylated+unmethylated) DNA in different cell lines, one can extrapolate the CpG methylation level at a given position. Overall, the data demonstrate that the bisulfite-PCR/LDR/Universal Array approach is a quantitative method for the measurement of DNA methylation.

Example 7

Tumor Specific LRAT Promoter Hypermethylation

The present invention demonstrates the identification of tumor specific LRAT promoter hypermethylation and correlation of methylation with cancer detection, diagnosis, and prognosis. Since aberrant DNA methylation may also result from aging, it is necessary to identify a promoter region where its methylation is disease specific. To determine if the alteration of methylation levels at LRAT promoter region is tumor specific, CRC tumor samples (n=133) and the adjacent normal tissues (n=69) were analyzed using bisulfite/PCR-PCR/LDR/Universal Array approach. For each clinical sample, the methylation levels of ten CpG dinucleotides within the 5'-UTR and exon-1 were interrogated.

Figure 15:
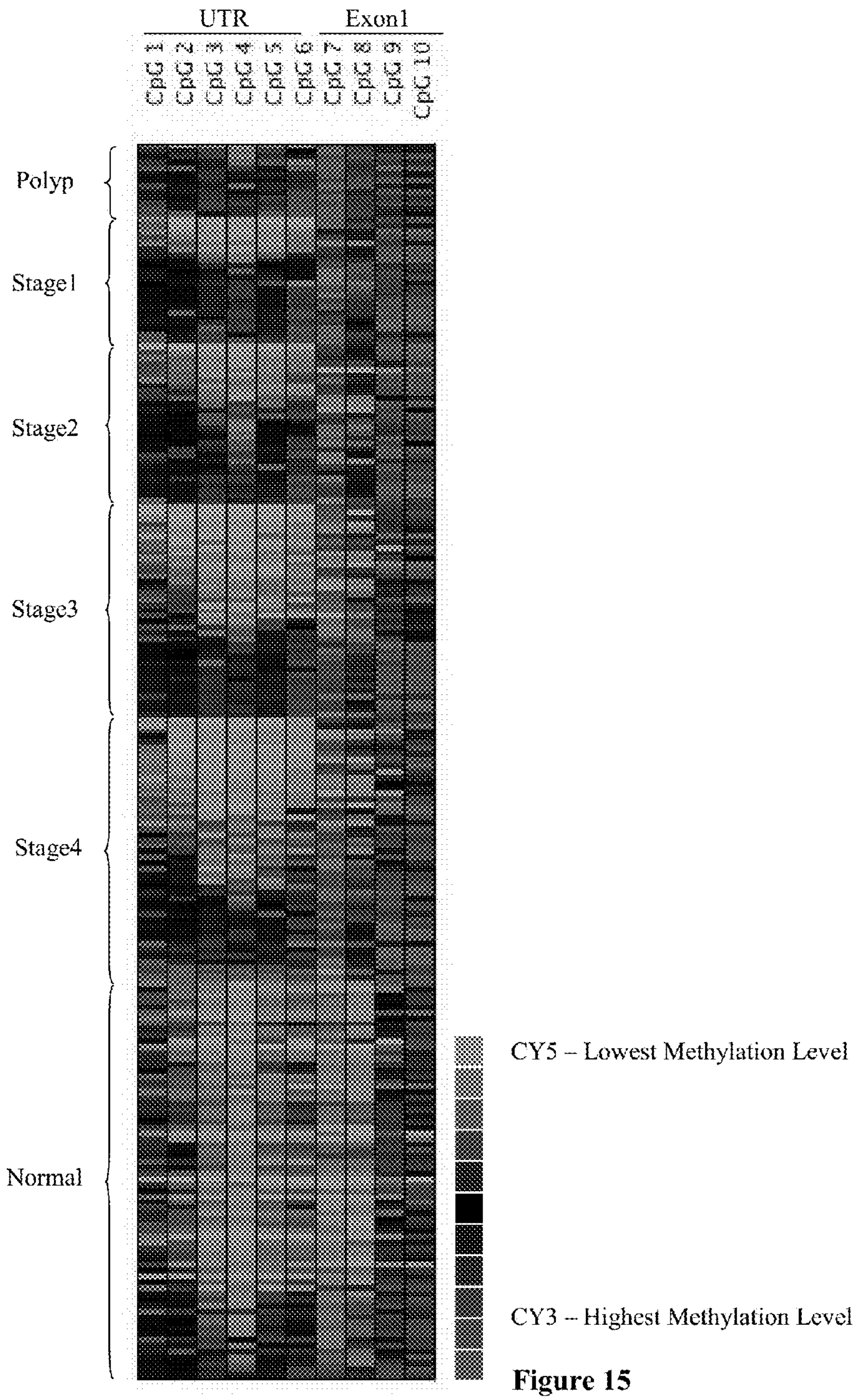
FIG. 15 represents the methylation profile of LRAT promoter regions among CRC samples and their matched normal tissues. Ten CpG dinucleotides were analyzed. CpG sites 1-6 are located in the 5'-UTR and CpG sites 7-10 are located in exon-1. Methylation levels are presented in a heat map format with a scheme from the highest methylation level to the lowest methylation level. The difference in methylation levels between CRC tumors and the matched normal tissues was observed at CpG sites 1-6 (5'-UTR). CpG sites 7-10 (exon-1) did not show tumor specific methylation changes.

As shown in FIG. 15, zero or low level cytosine methylation was observed in CpG sites 1-6 in the matched normal tissues, while medium to high level methylation of the same CpG sites was observed in CRC tumor samples. The CpG sites 1-6 are located in the 5'-UTR of the LRAT promoter. The difference in methylation level between these two types of tissues indicates that tumor specific LRAT DNA methylation occurred within the promoter sequences. There is no significant methylation change of CpG sites 7-10 either between the tumor samples or comparing with the adjacent normal tissues (low and high level methylation were associated with sites 7, 8 and 9, 10, respectively). The lack of difference in methylation level among these sites indicates that tumor-specific differential methylation is not present in LRAT exon-1 region where CpG sites 7-10 are located.

A typical example of quantitative methylation data obtained using bisulfite/PCR-PCR/LDR/Universal Array is shown in FIG. 16. LRAT methylation levels were analyzed from CRC samples of primary colorectal carcinoma, normal colon mucosa, and metastatic tissues (liver and lung). Ten CpG dinucleotide sites residing in the 5'-UTR (CpG sites 1-6) and exon-1 (CpG sites 7-10) regions of LRAT promoter were interrogated. Since the tumor (disease) specific aberrant methylation was identified in the 5'-UTR, the methylation levels of CpG sites 1-6 were averaged (the mean value) to determine the overall promoter methylation status. A promoter with a mean value of methylation signal intensity greater than 0.2 was scored as hypermethylated (methylation score 1), while a mean value equal to or less than 0.2 was scored as unmethylated (methylation score 0). This approach allowed a simple scoring system to use quantitative methylation data from multiple representative CpG sites across a larger DNA sequence region. Such quantitative reports give non-ambiguous and repeatable results of study DNA methylation.

To test the possibility of using LRAT promoter methylation as a prognostic and diagnostic marker, a series of 133 CRC patients were identified from Memorial-Sloan Kettering Cancer Center tumor bank and their tumor samples were subject to bisulfite/PCR-PCR/LDR/Universal Array analysis. The methylation levels of ten CpG dinucleotide sites in the LRAT promoter region were determined for each CRC sample. The average methylation level of CpG sites 1-6 was used to score the overall LRAT promoter methylation status (as described in FIGS. 15 and 16). A hypermethylated promoter was defined as having an average methylation level greater than 0.2.

As shown in FIG. 17, the analyzed clinical samples consisted of microsatellite instable (MSI) (n=40), non-MSI (polyps, n=13; stage I, n=15; stage II, n=15; stage III, n=21; stage IV, n=29), metastatic tumors (n=26), and normal colon mucosa tissues (n=69). LRAT promoter hypermethylation was associated with the majority of CRC tumors (92.5%) having a MSI phenotype. MSI and non-MSI tumors are two distinct subtypes of CRC. MSI patients typically have better survival and clinically favorable outcomes. The data also indicates that a high percentage CRC polyps (92.3%) are associated with hypermethylation of the LRAT promoter. A bowel polyp (adenoma) is a small growth that forms on the inside lining of the colon or rectum. About 1 in 4 people over the age of 50 develop at least one bowel polyp. Polyps are usually benign and considered the initial step during CRC development. A benign polyp may turn cancerous and this change usually takes place after a number of years. Hypermethylation of LRAT gene promoter was also seen in samples with CRC stages I (66.7%), II (66.7%), III (33.3%) and IV (41.4%). However, the normal colon mucosa tissues were methylated at relatively low percentage (~18%) in these patients.

The consistency of observing hypermethylation of the LRAT promoter in clinically favorable cohorts (i.e. MSI, polyps, stages I and II), but not in the advanced CRC samples (i.e. stages III and IV) has indicated the association between LRAT promoter hypermethylation and CRC development and progression.

A greater percentage of LRAT promoter hypermethylation was found in earlier (I and II) than in the later (III and IV) CRC stages. CRC is pathologically divided into four distinct clinical stages based on the degree of abnormal cells infiltrating the bowl wall tissue. Stages I and II are tumors retained between mucosa and muscle layers without involving lymph nodes and other tissues. A greater than 70-75% survival rate has been reported for patients in these categories. A larger percentage of the samples analyzed in stages I (66.7% in 15 cases) and II (66.7% in 15 cases) showed LRAT promoter hypermethylation. In stages III and IV, the tumor cells are no longer retained between mucosa and muscle layers but have spread to lymph nodes and other tissues. A less than 65-35% survival rate has been reported for patients in these categories. A reduced percentage of LRAT promoter hypermethylation was seen in stages III (33.3% in 21 cases) and IV (41.4% in 29 cases).

Figure 19:
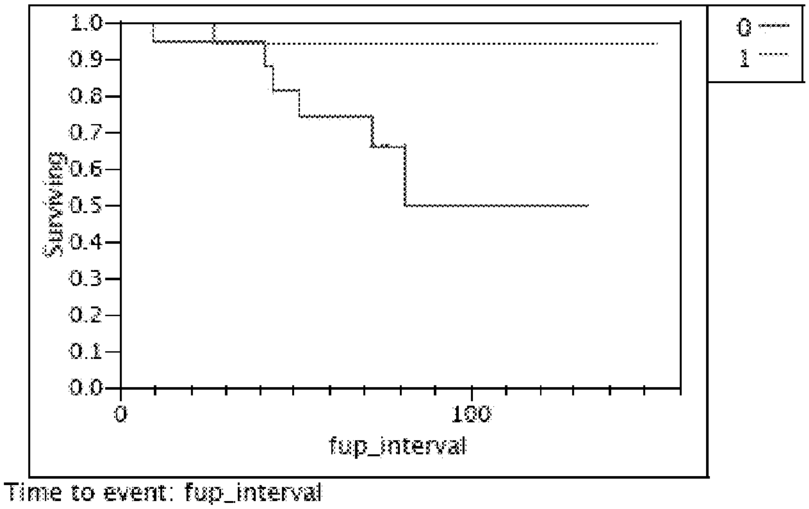
FIG. 19 shows the disease specific Kaplan-Meier survival analysis. CRC tumor samples of clinical stages II and III were included in the survival analysis. Data were stratified by Bisulfite/PCR-PCR/LDR/Universal Array assay. The Log-Rank test has shown a Chi-Square=4.44 and P=0.035.

LRAT promoter methylation is significantly associated with increased survival for all CRC patients. When all four CRC stages were considered, patients with LRAT promoter hypermethylation had a better disease-specific survival rate than patients with unmethylated promoter (FIG. 18). Only 12 of 39 (30.8%) individuals with LRAT promoter hypermethylation had died within the study period, whereas 23 of 42 (54.8%) individuals with unmethylated LRAT promoter had died. Log rank test was used to compare the two survival curves produced from methylated and unmethylated LRAT groups (p=0.0296). Since the MSI patients typically have a better survival and clinical outcome, the present Kaplan-Meier survival analysis was performed on patients with non-MSI genotype. When only tumors in the stages II and III were considered, a better disease-specific survival was also observed in patients with LRAT promoter hypermethylation (FIG. 19). Only 1 of 17 (5.9%) individuals in this cohort with LRAT promoter hypermethylation had died within the study period, while 6 of 19 (31.6%) individuals who died had unmethylated LRAT promoter regions. Statistical significance was achieved using the log rank test of the two survival curves produced from methylated and unmethylated LRAT groups ($p=0.035$). Survival was measured from the date of resection of colorectal cancer to the date of death, the completion of 5 years of follow-up, or the last clinical review before April 2006. Only cancer-related deaths were analyzed as events. A p-value of less than 0.05 was considered as statistical significance.

Example 8

Quantitative Analysis of LRAT mRNA

Real-time quantitative PCR was carried out in a reaction mixture containing TaqMan® Universal PCR Master Mix (Applied Biosystems, Foster City, Calif.), 20× TaqMan® Gene Expression Assay Mix (Applied Biosystems, Foster City, Calif.), 50 ng of cDNA in a final volume of 20 ul. Real-time PCR was run on an ABI PRISM 7500 system with the protocol of 10 minutes at 95° C., and then cycled for 40 rounds of 95° C. for 15 seconds and 60° C. for one minute. GAPDH was used as an endogenous control for all measurements. Each sample was measured in triplicate and the average $C_T$ (threshold cycle) value was used for calculating mRNA expression levels using the comparative $C_T$ method of quantitative analysis. The $C_T$ is the cycle number at which the fluorescence generated within a reaction crosses the threshold line.

Example 9

Tumor Specific LRAT mRNA Expression

Figure 20:
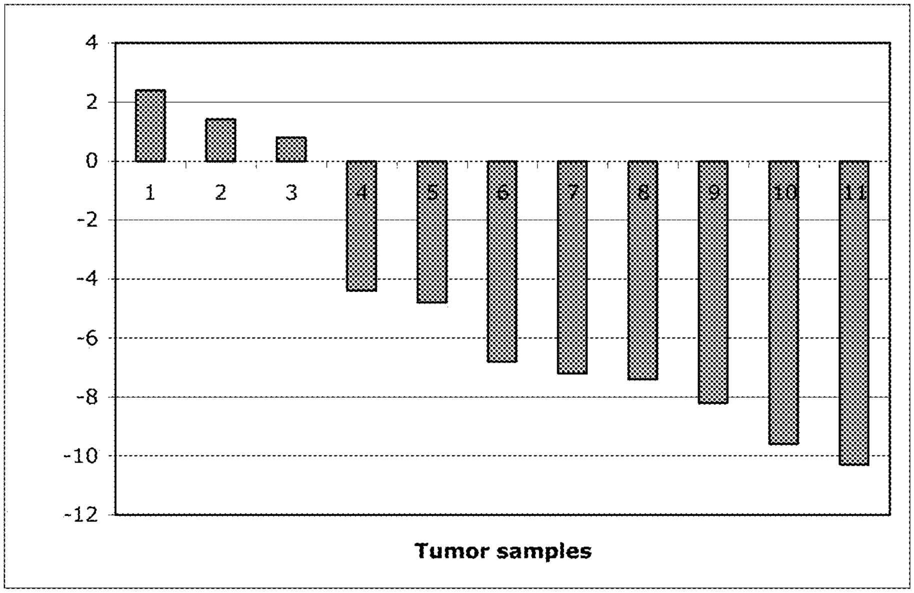
FIG. 20 shows the quantitative TaqMan analysis of LRAT mRNA levels in colorectal cancer and the matched normal mucosa tissues. GAPDH was used as an endogenous control for each sample. The Y-axis represents the Log 2 based ΔΔCt values, which indicates the differences of LRAT mRNA levels between CRC tumor and the matched normal tissues. For example, paired sample No. 4 has a $Log_2(\Delta\Delta Ct) \approx -5$, which is equivalent to $\Delta\Delta Ct \approx -32$. This value represents a 32-fold decrease in the level of LRAT mRNA expression in the tumor tissue compared to the normal mucosa tissue counterpart.

There is a correlation between LRAT promoter hypermethylation and LRAT mRNA expression. The experiments were performed using paired. CRC tumors with the matched normal mucosa. As shown in FIG. 20, a total of 11 paired samples were chosen for the study. The sample selection criteria was based on the presence of hypermethylated LRAT promoter in the tumors but not in the matched normal mucosa. TaqMan quantitative PCR assays were used to quantitatively determine the LRAT RNA expression of each paired samples. Each sample was measured in triplicates and the average $C_T$ (threshold cycle) value was used for calculating mRNA expression levels. The $C_T$ is the cycle number at which the fluorescence generated within a reaction crosses the threshold line. $C_T$ values are logarithmic and are used either directly (comparative $C_T$ method) or indirectly (interpolation to standard curves to create linear values) for quantitative analyses. The comparative $C_T$ method (ΔΔCt) was used for quantitative relative gene expression analysis. The calculation of ΔCt was based on the $C_{T(LRAT,tumor)}-C_{T(GAPDH,tumor)}$ and $C_{T(LRAT,normal)}-C_{T(GAPDH,normal)}$. The ΔΔCt was calculated by $(C_{T(LRAT,tumor)}-C_{T(GAPDH,tumor)})-(C_{T(LRAT,normal)}-C_{T(GAPDH,normal)})$. Eight pairs of samples have shown the ΔΔCt≥5, which indicates a greater than 32-fold decreases in LRAT mRNA expression in the tumor (hypermethylated LRAT) compared to normal (unmethylated LRAT) tissues. Three sample pairs showed the ΔΔCt≤2, which indicate a small change or no change in the RNA levels between the matched tumor and normal tissues. The discrepancy of these later cases was due to the poor quality of isolated total mRNA as starting assay material.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method comprising:

providing a colorectal cancer sample from a human subject;

determining in the provided sample from the subject a first methylation level of lecithin:retinol acyl transferase gene promoter having a nucleotide sequence corresponding to the nucleotide sequence of SEQ ID NO: 1;

providing a second methylation level of the lecithin:retinol acyl transferase gene promoter having a nucleotide sequence corresponding to the nucleotide sequence of SEQ ID NO: 1, said second methylation level being from either (1) a colorectal sample obtained from the subject at a time before said determining, or (2) one or more reference samples obtained from early stage colorectal tumors or benign colorectal tissue;

comparing the first methylation level of the lecithin:retinol acyl transferase gene promoter nucleotide sequence with the second methylation level of the lecithin:retinol acyl transferase gene promoter nucleotide sequence detecting a decrease in the first methylation level compared to the second methylation level; and administering a pharmaceutical composition comprising a lecithin:retinol acyl transferase inhibitor to the subject based on said detecting.

2. The method according to claim 1, wherein the methylation level of one or more of a plurality of target lecithin:retinol acyl transferase gene promoter nucleotide sequences within the provided sample is quantified, said method comprising:

measuring the number of CpG nucleotides which are methylated at a defined site within the promoter and measuring the number of CpG nucleotides which are unmethylated at the defined site within the promoter, whereby a quantitative measure of the methylation level at a defined CpG site in sample containing a plurality of lecithin:retinol acyl transferase gene promoter nucleotide sequences is determined by the ratio of site specific methylated CpG nucleotides to the sum of the site specific methylated and unmethylated CpG nucleotides.

3. The method according to claim 1, wherein the methylation level of one or more of a plurality of target lecithin:retinol acyl transferase gene promoter nucleotide sequences within the provided sample is quantified, said method comprising:

determining the level of methylation at individual CpG sites within the lecithin:retinol acyl transferase gene promoter nucleotide sequence and calculating an average level of methylation across the individual CpG sites located within the lecithin:retinol acyl transferase gene promoter nucleotide sequence, wherein said average indicates the overall level of lecithin:retinol acyl transferase promoter nucleotide sequence methylation.

4. The method according to claim 1, wherein the methylation level of the lecithin:retinol acyl transferase gene promoter nucleotide sequence is determined by analysis of one or more of the CpG nucleotide sites within nucleotides 1-296 of SEQ ID NO:1.

5. The method according to claim 4, wherein the methylation level of the lecithin:retinol acyl transferase gene promoter nucleotide sequence is determined at nucleotides 114, 172, 222, 242, 263, 279, or a combination thereof, in SEQ ID NO:1.

6. The method of claim 1, wherein said determining comprises:

subjecting the sample to a bisulfite treatment to convert, unmethylated cytosine residues, but not methylated cytosine residues, into uracil residues;

providing one or more primary oligonucleotide primer sets, each set characterized by (a) a first oligonucleotide primer, having a lecithin:retinol acyl transferase gene promoter target-specific portion and a 5' upstream universal primer-specific portion, wherein the lecithin:retinol acyl transferase gene promoter target-specific portion is suitable for hybridization on a first strand of the lecithin:retinol acyl transferase gene promoter in which unmethylated cytosines have been converted to uracil, and (b) a second oligonucleotide primer, having a lecithin:retinol acyl transferase gene promoter target-specific portion and a 5' upstream universal primer-specific portion, wherein the lecithin:retinol acyl transferase gene promoter target-specific portion is suitable for hybridization on a polymerase extension product of the first strand;

subjecting a primary polymerase chain reaction mixture, comprising the sample, the primary oligonucleotide primer set, and a polymerase, to two or more polymerase chain reaction cycles comprising a denaturation treatment, wherein hybridized nucleic acid sequences are separated, a hybridization treatment, wherein the target-specific portions of the primary oligonucleotide primer sets hybridize to the lecithin:retinol acyl transferase gene promoter target nucleic acid molecules with unmethylated cytosines converted to uracil or to extension products of such modified target nucleic acid molecules, and an extension treatment, wherein the hybridized primary oligonucleotide primers are extended to form primary extension products complementary to the lecithin: retinol acyl transferase gene with unmethylated cytosines converted to uracil;

providing a universal oligonucleotide primer set characterized by (a) a first universal primer containing the 5' upstream portion of the first oligonucleotide primer of the primary oligonucleotide primer set, and (b) a second universal primer containing the 5' upstream portion of the second oligonucleotide primer of the primary oligonucleotide primer set;

subjecting a secondary polymerase chain reaction mixture, comprising the primary extension products, the secondary universal oligonucleotide primer set, and the polymerase, to two or more polymerase chain reaction cycles comprising a denaturation treatment, wherein hybridized nucleic acid sequences are separated, a hybridization treatment, wherein the secondary oligonucleotide primers hybridize to the primary extension products, and an extension treatment, wherein the hybridized secondary oligonucleotide primers are extended to form secondary extension products complementary to the primary extension products;

providing a plurality of oligonucleotide probe sets, each set characterized by (a) a first oligonucleotide probe, having a secondary extension product-specific portion and a detectable reporter label, and (b) a second oligonucleotide probe, having a secondary extension product-specific portion, wherein the oligonucleotide probes in a particular set are suitable for ligation together when hybridized on a complementary secondary extension product, but have a mismatch which interferes with such ligation when hybridized to any other nucleic acid molecule present in the sample;

subjecting a ligase detection reaction mixture, comprising the secondary extension products, the plurality of oligonucleotide probe sets, and a ligase, to one or more ligase detection reaction cycles comprising a denaturation treatment, wherein any hybridized oligonucleotides are separated from the secondary extension product, and a hybridization treatment, wherein the oligonucleotide probe sets hybridize in a base-specific manner to their respective secondary extension products, if present, and ligate to one another to form a ligation product containing (a) the detectable reporter label and (b) the secondary extension product-specific portions connected together, wherein the oligonucleotide probe sets may hybridize to other nucleic acid molecules but do not ligate together due to a presence of one or more mismatches and individually separate during the denaturation treatment; and detecting the reporter labels of the ligation products, thereby indicating the promoter methylation level of the lecithin:retinol acyl transferase gene promoter nucleotide sequence in the sample.

7. The method according to claim 6, wherein the bisulfite treatment is catalyzed by hydroquinone and is carried out under cycling conditions to periodically dissociate both strands of nucleic acid molecules in the sample.

8. The method according to claim 6, wherein the oligonucleotide primers of the primary oligonucleotide primer set contain degenerate positions or nucleotide analogues to permit hybridization of the first and second oligonucleotide primers of the primary oligonucleotide primer set to the target nucleic acid molecule independent of the target nucleic acid molecule's methylation status.

9. The method according to claim 8, wherein the oligonucleotide primers of the primary oligonucleotide primer set contain a nucleotide analogue selected from the group consisting of 2-dimethylaminomethyleneamino-6-methyoxyaminopurine (dK), 6H,8H-3,4-dihydro-pyrimido[4,5-c][1,2]oxazin-7-one (dP), 3-nitropyrrole, 5-nitroindole, and inosine.

10. The method according to claim 6, wherein the oligonucleotide primers of the primary oligonucleotide primer set are selected from the group consisting of SEQ ID NOs: 3, 4, 5, and 6.

11. The method according to claim 6, wherein the oligonucleotide probe sets for the ligation detection reaction are selected from the group consisting of SEQ ID NOs: 8, 9, 10, 11, 12, 13, 14, 15, 16, 17, 18, 19, 20, 21, 22, 23, 24, 25, 26, 27, 28, 29, 30, 31, 32, 33, 34, 35, 36, and 37.

12. The method according to claim 6, wherein multiple secondary extension products are pooled prior to said subjecting the ligase detection reaction mixture to one or more ligase detection reaction cycles.

13. The method according to claim 6, wherein the ligation products of the oligonucleotide probes in a particular set have a unique length so that they can be distinguished from other nucleic acid molecules in the ligase detection reaction mixture, said detecting comprising:

separating the ligation products by size or electrophoretic mobility and distinguishing the ligation products which differ in size.

14. The method according to claim 6, wherein the ligation products of the oligonucleotide probes contain an addressable array-specific portion, said detecting further comprising:

providing a solid support with different capture oligonucleotide probes immobilized at different particular sites, wherein the capture oligonucleotides are complementary to the addressable array-specific portions; and contacting the ligase detection reaction mixture, after said subjecting it to one or more ligase detection reaction cycles, with the solid support under conditions effective to hybridize the ligation products to the capture oligonucleotide probes in a base-specific manner, thereby capturing the addressable array-specific portions to the solid support at the site with the complementary capture oligonucleotide.

15. The method according to claim 6, wherein the ligation products of the oligonucleotide probes contain unique 5'-reporter labels whereby the ligation products containing a methylated cytosine can be distinguished from ligation products containing unmethylated cytosine using a reporter detection system.

16. The method of claim 15, wherein the 5'-reporter label is selected from the group consisting of chromophores, fluorescent moieties, enzymes, antigens, heavy metals, magnetic probes, infrared dyes, phosphorescent groups, radioactive materials, chemiluminescent moieties, and electrochemical detecting moieties.

* * * * *

SEQUENCE LISTING

<160> NUMBER OF SEQ ID NOS: 37

<210> SEQ ID NO 1
<211> LENGTH: 950
<212> TYPE: DNA
<213> ORGANISM: Homo sapiens

<400> SEQUENCE: 1
gcccccaggt gcgctccttc tccggctgct tgtagcactg gtctcactgt ccccgccgtc 60
agccaccggt tccttatccg tctcattccc cattgtggct tggctgagcc ggtcgccagg 120
cctcgctgtc ctcctttgcc ttcctctctc ctcagcggcc gtactttgcg ccgtacctca 180
cctggcctgc aggtgagcag cagcgcagca cccctgcccg gcgagcttaa cttgcccagc 240
ccggcccctg ccggagtggc accggcacct ctccaagacg ccctcttccc tgcaggatga 300
agaaccccat gctggaggtg gtgtctttac tactggagaa gctgctcctc atctccaact 360
tcacgctctt tagttcgggc gccgcgggcg aagacaaagg gaggaacagt ttttatgaaa 420
ccagctcttt ccaccgaggc gacgtgctgg aggtgccccg gacccacctg acccactatg 480
gcatctacct aggagacaac cgtgttgccc acatgatgcc cgacatcctg ttggccctga 540
cagacgacat ggggcgcacg cagaaggtgg tctccaacaa gcgtctcatc ctgggcgtta 600

-continued

```
ttgtcaaagt ggccagcatc cgcgtggaca cagtggagga cttcgcctac ggagctaaca    660

tcctggtcaa tcacctggac gagtccctcc agaaaaaggc actgctcaac gaggaggtgg    720

cgcggagggc tgaaaagctg ctgggcttta ccccctacag cctgctgtgg aacaactgcg    780

agcacttcgt gacctactgc agatatggca ccccgatcag tccccagtcc gacaaggtat    840

gatgtgtgac tcccagggga agtgggctcc gcggagatgc cccctcccat ccctgacctt    900

ttctcttccc cgcgagtagg gatctaattc ctggacacct cccctaccac               950


<210> SEQ ID NO 2
<211> LENGTH: 4393
<212> TYPE: DNA
<213> ORGANISM: Homo sapiens

<400> SEQUENCE: 2

agtttagaaa accaaatttc tcaggcctag agctcaagta aaagaaaatc tgagataatg     60

aagtctggaa cactgggcct gcattctgct cctgactctg tgcccttggg taagacattg    120

aacttcccca ccccagattc atcctacacc ctaaggaggg tgtaggattt tgtagccttc    180

ctagtgatgg catactatta atcagaacct taaccagctc tattctcact atcccagtaa    240

aatgatgtta aaaattagac ctcgtgacat gagagaagag gggaaattaa ttacagatta    300

caaagaaatt gtgggatcta agtttagggt gaggtgtttt attgaacctc tagggttggt    360

catagcacct gccatatagc aggtattcaa taaatgatgt gtaatgggtg gttagactga    420

tggaaaggca ggccttccca gtgacggtaa aggacctggg gcaaaagaga cctgtggttg    480

agtcctgatc cccacacatt agcacactga ctagacgaag ttataagctt caatttcttc    540

ctgtgtaaaa tggagataat acctcatagg gttatgagga ttaaataaga aaatgcttag    600

ttcagtgcct aatacacagg aagcacaccg taaatattag ttattattat tactaatact    660

gtgatcatat cttccatcca aagacttctc tgaggagcag ggggcatcca gagataaaaa    720

gcctgcaggt gggaaatctg ttagccttct agggcgttag gtttctgtgg aactctgcac    780

ctcttccctg tcctagttct taagaacaga aactctccag ggacctctgg tgaggtagcc    840

gtgggaagat gaggtgcaga agtaagctgg gacctgtgag cctcaatttc ggcctcttct    900

gcgctgagac ccaagcggat cttgcttggc ctgtatgcgt tactggggga aatggacgtg    960

ggcctgagcg cggcaggtgc gagggcgctg ccccggggcc gaccaccctg cggggacact   1020

gtagctgtca ttccttcttc tgcaggcggg taggggaagc ggtggccaaa gtgggagtcg   1080

accgctcagc acagtctgtc tgagtgttga ccaggaaagt ccaggctctt tctaaatctc   1140

gccgccagac ctggtgacgc attcgcatgt atttaaggcg tttgcacgca gaacgttatc   1200

acagaatgta gccacctttc ttaacggtcc gggaaaccag aggtctctcc agctactcag   1260

ggtagaggaa tttctcctat ctccatgtga catcttctga tttagaagaa ctaatgttag   1320

atttctcttg ggcctttcca cctacagcta tagtcttccc tttgtttagc taaaattgag   1380

gcaggtagga aaatattatt gggggcataa gcctattagt gtgtaaacgt atttttatga   1440

agtgtgcctc cagggagcca ttaaaaactg acctctcaac cacagaaata gatgagattt   1500

tgagaacatt gagaagctgc cttttgcaaa gtaaatttgc aatggtcctt gacgaagggg   1560

ggtcgggggc ggggagaagt ccagccgaga gaggagctca ttccacgcta tatttttgca   1620

gttgaaaagc tgcctaatca tcgctaaccg cttcccgcat aagagttctg ggaagacttc   1680

agaaacaagg caaatgaaga cttttcactg cctccttcgg gctgtcgctt ccggaagccg   1740
```

-continued

```
aagtcctagc acgcagagca gcaggagagg gttactttca ggcaattcca ctgagcaaaa   1800
taaatcactt aatggcataa cgttctggct taaaaaattg gaatttatca gaggcaaaaa   1860
tatccttcaa gaaactatgg acactccgcg ccctattcat ttccatggca gcagagtatc   1920
tgcatcttga gccacctata cagattcatg cctcgtatcg ctctcacctc ctttcttttt   1980
gaagtaaagc cctttcccaa gaaggcggcc agaaagtgga ccccaccggg ggaaaaagaa   2040
aaatgaaacg caaatcagct tggcactgct tgcgtcttcc aaaacgcggt gggacaaggc   2100
tattgagtct atagctaatt ctttcatgta tataaaatgt atacatatgt atatattttt   2160
atatacataa aagaattcat atatatgtat atagctatgt ggagccctga agcaattctc   2220
catgcttttg tctccctcaa gttccccagg tggaggcagt cataagcatt ataagccgcc   2280
ttagtgacca ccagggacgg aaaccgttaa ttatcacgtt tcctttcatc tccaggggcc   2340
ctttggcccg tgacacaaga ggcttcggta ttggcgcttt cccagaactg gcccagagga   2400
gccagttcag agtgtgaggt cgggtctgca ttgaacgtac acaccgaggt ctatcagact   2460
cccccgattt tagcgaaggg tgctgactgc tgtgctgcta gaggctagca agctccctgt   2520
gcgcagctga tgagtttcag caactcgcca cctgggcgct tttctttaaa ttttgggagt   2580
aaactgggaa aataaaaaaa tctccacgtc cactggctct ctccccttct ccaacttcct   2640
ctttcgactc gtttgtggga gttttctcct ctttgctggg actataatgt gatgcgcaat   2700
cgtttgtgaa tgaacaaaag tcaccggcaa gcagggagac ggggacagat cgctgacggc   2760
agattgaggg tggcagcaaa ggcccggcct ccaaggataa tggggagccg ttttccctca   2820
cgcctggtct ctatggcccc cttcgtcttc caggtaaaat gaatgttcct tcatccatca   2880
tccgcagagt accctcaggc gtgcgtagaa tctgctgatg aaacctatta gcgccgactg   2940
ggcagctttg tggagccacc cgaggctctc cattgtggcc tttgtctgca gaatttaagc   3000
atttacataa tgcattagca cggaactcag cacccggtgg ggacatcgcg tgccaagcct   3060
ggcgcggcca acgcttcagc ggctccctca cccggcagct ccctaggacc accctcgagg   3120
aggcattgga gtcgggctgc aggcgcacgg gcaaagaact tagcatctca tccaagtact   3180
tcgccttcct tggccgtctc cgggaggtta tgcttaaaaa cataaaaata aaaataaaaa   3240
taaaaataaa gggaggcgga caaagtttcg gtgggtgaac tgaagctggg tccatgtgac   3300
cctgaagccg gagaaataaa cttaacatga atcttgcttt cctggcgggc gttgggaccc   3360
cgccgttttt catgccaacc gttggaagct tcgtactcaa cggccacagg tgcctaggag   3420
cgcagagagg cctcgggttc aaatcaccgg cgcgcaggga ctggactcgc gggtagcgac   3480
ccccccaacc cccccccccc cgccctacac acacaccctc gcgccggctg aaagcatgga   3540
ggattcaggg catttgaaaa aagaggggct gggcgcggtg gctcacgcct gtaatcccag   3600
cggtttggga ggtccagaag ggcggatcac ttgaggtcag gagttcgaga ccagcctggc   3660
caacaccagc ctggccaaca tggtgagacc ccgtgtctac taaaaataca aaaattagcc   3720
aggcgtggtg cctgtaatat cagctacttg ggaggctgag gcacgagaat cgcttgaacc   3780
tgggaggcgg aggttgcagt gagcccagat cgcgccaccg ccctcctgct ctgggtgata   3840
gagcaaggca ctgtctcaaa acaaaacaaa acaaaacgaa agattcggtc aggaaagaat   3900
ctgcaggcat tcgaggcgct cgcactttgc aaagtaaatg caatctcttt attaagccga   3960
agtccctcat atctatcctt ttagaggaag gtggtccaac tcagaaatct ctcccaagag   4020
gactttccac cgaagactac cgcgaagtgc caggaactcg ccccagtccc gacaggtgca   4080
ggacctttcg tgccgccaca ccttgggact ctacctccct aaataggcca cttaaaagcc   4140
```

-continued agtagtgcaa ccgggatccc gcggcgataa agaatcactg tgcagaaccc tggagctggg 4200
agtcggcccg cccccctccc aaagaaaccg ggatcccgcg tcctccccgc cgctagcgca 4260
gcgcgccagc ggcgcccaat cagtgagctt tccgggtctg tgacggcctt cggctccgcc 4320
ccctcgacgg ccataaaaag tcgcagcgaa gcctgcacct ccgagcaccg cgcgcggccc 4380
tgcccccggc acg 4393

<210> SEQ ID NO 3
<211> LENGTH: 49
<212> TYPE: DNA
<213> ORGANISM: Artificial
<220> FEATURE:
<223> OTHER INFORMATION: primer

<400> SEQUENCE: 3
cgctgccaac taccgcacat cttatttttt attgtggttt ggttgagtc 49

<210> SEQ ID NO 4
<211> LENGTH: 49
<212> TYPE: DNA
<213> ORGANISM: Artificial
<220> FEATURE:
<223> OTHER INFORMATION: primer

<400> SEQUENCE: 4
cgctgccaac taccgcacat cacctccaac ataaaattct tcatcctac 49

<210> SEQ ID NO 5
<211> LENGTH: 51
<212> TYPE: DNA
<213> ORGANISM: Artificial
<220> FEATURE:
<223> OTHER INFORMATION: primer

<400> SEQUENCE: 5
cgctgccaac taccgcacat cataatcgtg ttgtttatat gatgttcgat a 51

<210> SEQ ID NO 6
<211> LENGTH: 51
<212> TYPE: DNA
<213> ORGANISM: Artificial
<220> FEATURE:
<223> OTHER INFORMATION: primer

<400> SEQUENCE: 6
cgctgccaac taccgcacat ccacaacaaa ctataaaaaa taaaacccaa c 51

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
cgctgccaac taccgcacat c 21

<210> SEQ ID NO 8
<211> LENGTH: 34
<212> TYPE: DNA
<213> ORGANISM: Artificial
<220> FEATURE:
<223> OTHER INFORMATION: probe -continued

<400> SEQUENCE: 8
tgttattttt tattgtggtt tggttgagtt ggtt 34

<210> SEQ ID NO 9
<211> LENGTH: 37
<212> TYPE: DNA
<213> ORGANISM: Artificial
<220> FEATURE:
<223> OTHER INFORMATION: probe

<400> SEQUENCE: 9
ttgttttttt tttttttag tggttgtatt ttgtgtt 37

<210> SEQ ID NO 10
<211> LENGTH: 34
<212> TYPE: DNA
<213> ORGANISM: Artificial
<220> FEATURE:
<223> OTHER INFORMATION: probe

<400> SEQUENCE: 10
ttttgtcgga gtggtattgg tattttttta agat 34

<210> SEQ ID NO 11
<211> LENGTH: 39
<212> TYPE: DNA
<213> ORGANISM: Artificial
<220> FEATURE:
<223> OTHER INFORMATION: probe

<400> SEQUENCE: 11
ggtttgtagg tgagtagtag tgtagtattt ttgtttggt 39

<210> SEQ ID NO 12
<211> LENGTH: 40
<212> TYPE: DNA
<213> ORGANISM: Artificial
<220> FEATURE:
<223> OTHER INFORMATION: probe

<400> SEQUENCE: 12
gtgtagtatt tttgtttggt gagtttaatt tgtttagttt 40

<210> SEQ ID NO 13
<211> LENGTH: 37
<212> TYPE: DNA
<213> ORGANISM: Artificial
<220> FEATURE:
<223> OTHER INFORMATION: probe

<400> SEQUENCE: 13
ttaatttgtt tagtttggtt tttgttggag tggtatt 37

<210> SEQ ID NO 14
<211> LENGTH: 38
<212> TYPE: DNA
<213> ORGANISM: Artificial
<220> FEATURE:
<223> OTHER INFORMATION: probe

<400> SEQUENCE: 14
tttatatgat gtttgatatt ttgttggttt tgatagat 38

<210> SEQ ID NO 15
<211> LENGTH: 37

-continued

<212> TYPE: DNA
<213> ORGANISM: Artificial
<220> FEATURE:
<223> OTHER INFORMATION: probe

<400> SEQUENCE: 15
gtagaaggtg gtttttaata agtgttttat tttgggt 37

<210> SEQ ID NO 16
<211> LENGTH: 35
<212> TYPE: DNA
<213> ORGANISM: Artificial
<220> FEATURE:
<223> OTHER INFORMATION: probe

<400> SEQUENCE: 16
gtattcgcgt ggatatagtg gaggattttg tttat 35

<210> SEQ ID NO 17
<211> LENGTH: 34
<212> TYPE: DNA
<213> ORGANISM: Artificial
<220> FEATURE:
<223> OTHER INFORMATION: probe

<400> SEQUENCE: 17
tagaaaaagg tattgtttaa tgaggaggtg gtgt 34

<210> SEQ ID NO 18
<211> LENGTH: 30
<212> TYPE: DNA
<213> ORGANISM: Artificial
<220> FEATURE:
<223> OTHER INFORMATION: probe

<400> SEQUENCE: 18
attttttatt gtggtttggt tgagtcggtc 30

<210> SEQ ID NO 19
<211> LENGTH: 28
<212> TYPE: DNA
<213> ORGANISM: Artificial
<220> FEATURE:
<223> OTHER INFORMATION: probe

<400> SEQUENCE: 19
ttttttttta gcggtcgtat tttgcgtc 28

<210> SEQ ID NO 20
<211> LENGTH: 31
<212> TYPE: DNA
<213> ORGANISM: Artificial
<220> FEATURE:
<223> OTHER INFORMATION: probe

<400> SEQUENCE: 20
tgtcggagtg gtatcggtat ttttttaaga c 31

<210> SEQ ID NO 21
<211> LENGTH: 34
<212> TYPE: DNA
<213> ORGANISM: Artificial
<220> FEATURE:
<223> OTHER INFORMATION: probe

<400> SEQUENCE: 21

-continued gtaggtgagt agtagcgtag tatttttgtt cggc 34

<210> SEQ ID NO 22
<211> LENGTH: 31
<212> TYPE: DNA
<213> ORGANISM: Artificial
<220> FEATURE:
<223> OTHER INFORMATION: probe

<400> SEQUENCE: 22
ttttgttcgg cgagtttaat ttgtttagtt c 31

<210> SEQ ID NO 23
<211> LENGTH: 31
<212> TYPE: DNA
<213> ORGANISM: Artificial
<220> FEATURE:
<223> OTHER INFORMATION: probe

<400> SEQUENCE: 23
tgtttagttc ggtttttgtc ggagtggtat c 31

<210> SEQ ID NO 24
<211> LENGTH: 35
<212> TYPE: DNA
<213> ORGANISM: Artificial
<220> FEATURE:
<223> OTHER INFORMATION: probe

<400> SEQUENCE: 24
atatgatgtt cgatattttg ttggttttga tagac 35

<210> SEQ ID NO 25
<211> LENGTH: 31
<212> TYPE: DNA
<213> ORGANISM: Artificial
<220> FEATURE:
<223> OTHER INFORMATION: probe

<400> SEQUENCE: 25
ggtggttttt aataagcgtt ttattttggg c 31

<210> SEQ ID NO 26
<211> LENGTH: 31
<212> TYPE: DNA
<213> ORGANISM: Artificial
<220> FEATURE:
<223> OTHER INFORMATION: probe

<400> SEQUENCE: 26
tcgcgtggat atagtggagg atttcgttta c 31

<210> SEQ ID NO 27
<211> LENGTH: 26
<212> TYPE: DNA
<213> ORGANISM: Artificial
<220> FEATURE:
<223> OTHER INFORMATION: probe

<400> SEQUENCE: 27
ggtattgttt aacgaggagg tggcgc 26

<210> SEQ ID NO 28
<211> LENGTH: 64
<212> TYPE: DNA
<213> ORGANISM: Artificial

<220> FEATURE:
<223> OTHER INFORMATION: probe

<400> SEQUENCE: 28
gttaggtttc gttgtttttt tttgtttttt ttttttttta gggaggctgc tgtcctttcg 60
atca 64

<210> SEQ ID NO 29
<211> LENGTH: 68
<212> TYPE: DNA
<213> ORGANISM: Artificial
<220> FEATURE:
<223> OTHER INFORMATION: probe

<400> SEQUENCE: 29
gtattttatt tggtttgtag gtgagtagta gcgtagtatt tttgacagcg tgttcgttgc 60
ttgcatca 68

<210> SEQ ID NO 30
<211> LENGTH: 57
<212> TYPE: DNA
<213> ORGANISM: Artificial
<220> FEATURE:
<223> OTHER INFORMATION: probe

<400> SEQUENCE: 30
gagtttaatt tgtttagttc ggtttttgtt ggattgcggg aactcacgag gtcgtat 57

<210> SEQ ID NO 31
<211> LENGTH: 57
<212> TYPE: DNA
<213> ORGANISM: Artificial
<220> FEATURE:
<223> OTHER INFORMATION: probe

<400> SEQUENCE: 31
ggtttttgtc ggagtggtat tggtattttt ttaatggcga tggtccactc gcaatca 57

<210> SEQ ID NO 32
<211> LENGTH: 60
<212> TYPE: DNA
<213> ORGANISM: Artificial
<220> FEATURE:
<223> OTHER INFORMATION: probe

<400> SEQUENCE: 32
ggtatttttt taagacgttt tttttttgt aggatggcac ggctcgatag gtcaagcttt 60

<210> SEQ ID NO 33
<211> LENGTH: 63
<212> TYPE: DNA
<213> ORGANISM: Artificial
<220> FEATURE:
<223> OTHER INFORMATION: probe

<400> SEQUENCE: 33
gttttttttt ttgtaggatg aagaatttta tgttggaggc atcgcacttc gctttggctg 60
att 63

<210> SEQ ID NO 34
<211> LENGTH: 55
<212> TYPE: DNA
<213> ORGANISM: Artificial
<220> FEATURE:

-continued

```
<223> OTHER INFORMATION: probe

<400> SEQUENCE: 34

gatatggggt gtacgtagaa ggtggttttt acaaggcacg tcccagacgc atcaa          55


<210> SEQ ID NO 35
<211> LENGTH: 63
<212> TYPE: DNA
<213> ORGANISM: Artificial
<220> FEATURE:
<223> OTHER INFORMATION: probe

<400> SEQUENCE: 35

gttattgtta aagtggttag tatttgcgtg gatatagtgg cacgggagct gacgacgtgt     60

caa                                                                   63


<210> SEQ ID NO 36
<211> LENGTH: 64
<212> TYPE: DNA
<213> ORGANISM: Artificial
<220> FEATURE:
<223> OTHER INFORMATION: probe

<400> SEQUENCE: 36

ggagttaata ttttggttaa ttatttggac gagttttttt agacgcaccg caacaggctg     60

tcaa                                                                  64


<210> SEQ ID NO 37
<211> LENGTH: 56
<212> TYPE: DNA
<213> ORGANISM: Artificial
<220> FEATURE:
<223> OTHER INFORMATION: probe

<400> SEQUENCE: 37

ggagggttga aaagttgttg ggttttattt ttcatcgctg caagtaccgc actcaa         56
```